(12) United States Patent
Jen et al.

(10) Patent No.: US 7,601,849 B1
(45) Date of Patent: Oct. 13, 2009

(54) NONLINEAR OPTICAL COMPOUNDS AND RELATED MACROSTRUCTURES

(75) Inventors: Kwan-Yue Jen, Kenmore, WA (US); Larry R. Dalton, Silverdale, WA (US); Hong Ma, Seattle, WA (US)

(73) Assignee: University of Washington, Seattle, WA (US)

( * ) Notice: Subject to any disclaimer, the term of this patent is extended or adjusted under 35 U.S.C. 154(b) by 547 days.

(21) Appl. No.: 10/212,473

(22) Filed: Aug. 2, 2002

Related U.S. Application Data

(60) Provisional application No. 60/309,686, filed on Aug. 2, 2001.

(51) Int. Cl.
*C07D 409/06* (2006.01)
*C07D 333/12* (2006.01)
*C07D 333/22* (2006.01)

(52) U.S. Cl. .............................. 549/59; 549/74; 549/77

(58) Field of Classification Search ................... 549/59, 549/74, 77, 29, 61, 66, 71, 81, 481, 491, 549/499, 500, 65, 68, 474, 484, 497
See application file for complete search history.

(56) References Cited

U.S. PATENT DOCUMENTS

| | | | |
|---|---|---|---|
| 5,432,286 A | 7/1995 | Cabrera et al. | |
| 5,514,799 A | 5/1996 | Varanasi et al. | |
| 5,676,884 A | 10/1997 | Tiers et al. | |
| 5,679,763 A | 10/1997 | Jen et al. | |
| 5,693,734 A | 12/1997 | Herzig et al. | |
| 5,718,845 A | 2/1998 | Drost et al. | |
| 5,738,806 A | 4/1998 | Beckmann et al. | |
| 5,804,101 A | 9/1998 | Marder et al. | |
| 5,808,100 A | 9/1998 | Momoda et al. | |
| 6,067,186 A | 5/2000 | Dalton et al. | |
| 6,184,540 B1 | 2/2001 | Chmii et al. | |
| 6,211,374 B1 | 4/2001 | Ippoliti | |
| 6,281,366 B1 | 8/2001 | Frigoli et al. | |
| 6,348,992 B1 | 2/2002 | Zhang et al. | |
| 6,361,717 B1 | 3/2002 | Dalton et al. | |
| 6,652,779 B1 * | 11/2003 | Zhang et al. | ................. 252/582 |
| 6,716,995 B2 * | 4/2004 | Huang et al. | ................... 549/62 |

FOREIGN PATENT DOCUMENTS

| | | |
|---|---|---|
| WO | WO 00/09613 A2 | 2/2000 |
| WO | WO 01/53746 A1 | 7/2001 |
| WO | WO 01/56462 A1 | 8/2001 |
| WO | WO 01/77749 A1 | 10/2001 |
| WO | WO 01/79750 A1 | 10/2001 |
| WO | WO 02/08215 A1 | 1/2002 |
| WO | WO 02/14305 A2 | 2/2002 |
| WO | WO 02/14305 A3 | 2/2002 |
| WO | WO 02/29488 A1 | 4/2002 |
| WO | WO 02/37173 A2 | 5/2002 |

OTHER PUBLICATIONS

Fahey, J. T.; Shimizu, K.; Frechet, J. M. J.; Clecak, N.; Willson, C. G., Journal of Polymer Science, Part A: Polymer Chemistry, 31(1), 1-11 (English) 1993.*
Storck, Winfried; Manecke, Georg, Makromolekulare Chemie, 176(1), 97-125 (German) 1975.*

* cited by examiner

*Primary Examiner*—James O Wilson
*Assistant Examiner*—Ebenezer Sackey
(74) *Attorney, Agent, or Firm*—Christensen O'Connor Johnson Kindness PLLC

(57) ABSTRACT

Nonlinear optically active compounds, macrostructures that include nonlinear optically active components, and devices including the macrostructures. The nonlinear optically active compounds include dendrimers having two or more nonlinear optically active components. In certain embodiments, the compounds and dendrimers are crosslinkable.

39 Claims, 18 Drawing Sheets

FIGURE 2A
Convergent:
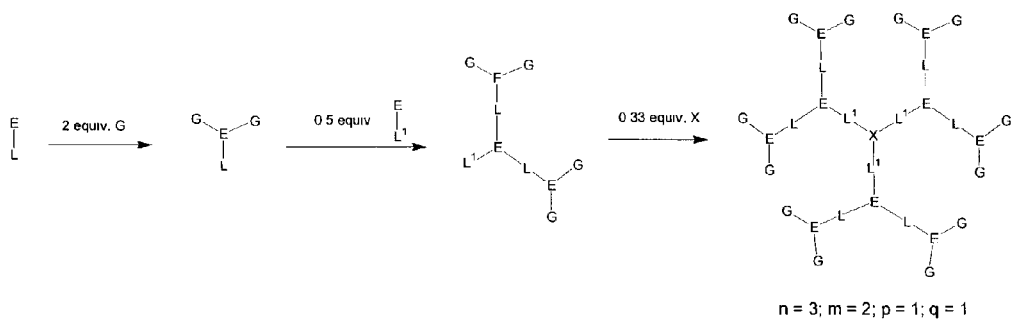
n = 3; m = 2; p = 1; q = 1
FIGURE 2B
Divergent:
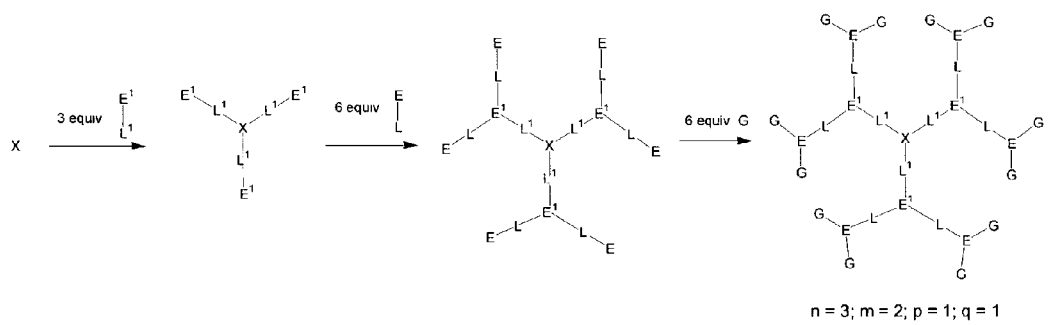
n = 3; m = 2; p = 1; q = 1
FIGURE 2C
Hybrid:
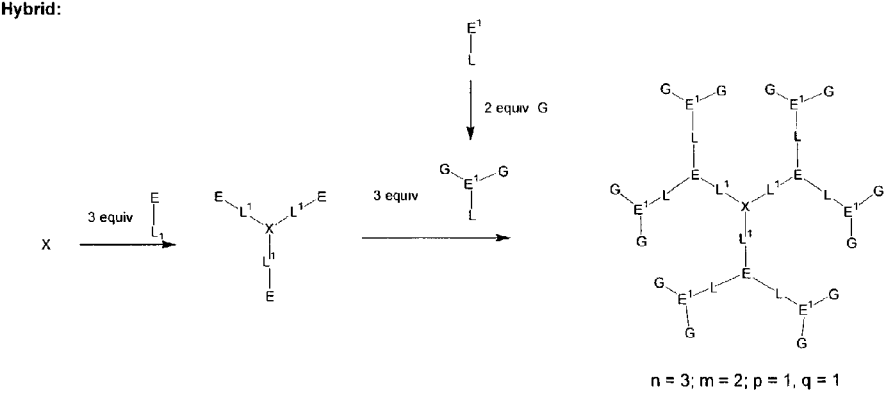
n = 3; m = 2; p = 1, q = 1
FIGURE 2

NONLINEAR OPTICAL COMPOUNDS AND RELATED MACROSTRUCTURES

CROSS-REFERENCE TO RELATED APPLICATION

This application claims the benefit of U.S. Provisional Application No. 60/309,686, filed Aug. 2, 2001, incorporated herein by reference in its entirety.

STATEMENT OF GOVERNMENT SUPPORT

This invention was made with government support under grant F49620-99-1-0287 awarded by the United States Air Force. The government has certain rights in the invention.

FIELD OF THE INVENTION

The present invention relates in general to nonlinear optically active compounds, macrostructures that include nonlinear optically active components, and devices including the macrostructures.

BACKGROUND OF THE INVENTION

Electrical signals can be encoded onto fiber-optic transmissions by electro-optic modulators. These modulators include electro-optic materials having highly polarizable electrons. When these materials are subject to an electric field, their polarization changes dramatically resulting in an increase in the index of refraction of the material and an accompanying decrease in the velocity of light traveling through the material. This electric field-dependent index of refraction can be used to encode electric signals onto optical signals. Uses include, for example, switching optical signals and steering light beams.

A variety of electro-optic materials have been utilized for use in electro-optic devices. Among these materials are inorganic materials such as lithium niobate, semiconductor materials such as gallium arsenide, organic crystalline materials, and electrically poled polymer films that include organic chromophores. A review of nonlinear optical materials is provided in L. Dalton, "Nonlinear Optical Materials," *Kirk-Othmer Encyclopedia of Chemical Technology*, 4$^{th}$ ed., Vol. 17 John Wiley & Sons, New York, pp. 288-302 (1995).

In contrast to inorganic materials in which polar optical lattice vibrations diminish effectiveness, the optical properties of organic nonlinear optical materials depend primarily on the hyperpolarizability of their electrons without a significant adverse contribution from the lattice polarizability. Thus, organic nonlinear optical materials offer advantages for ultrafast electro-optic modulation and switching.

Lithium niobate, a common material currently utilized in electro-optic devices, has an electro-optic coefficient of about 35 pm/V resulting in a typical drive voltage of about 5 volts. Drive voltage ($V_\pi$) refers to the voltage that produces a $\pi$ phase shift of light. Lithium niobate has a high dielectric constant ($\in=28$), which results in a mismatch of electrical and optical waves propagating in the material. The mismatch necessitates a short interaction length, which makes drive voltage reduction through increasing device length unfeasible, thereby limiting the device's bandwidth. Recent lithium niobate modulators have been demonstrated to operate at a bandwidth of over 70 GHz.

Electro-optic poled polymers have also been utilized as modulating materials. Their advantages include their applicability to thin-film waveguiding structures, which are relatively easily fabricated and compatible with existing microelectronic processing. These polymers incorporate organic nonlinear optically active molecules to effect modulation. Because organic materials have low dielectric constants and satisfy the condition that $n^2=\in$, where n is the index of refraction and $\in$ is the dielectric constant, organic electro-optic will have wide bandwidths. The dielectric constant of these materials ($\in=2.5$-$4$) relatively closely matches the propagating electrical and optical waves, which provides for a drive voltage in the range of about 1-2 volts and a bandwidth greater than 100 GHz.

Advantages of organic nonlinear optical materials include a bandwidth in excess of 100 GHz/cm device and ease of integration with semiconductor devices. See L. Dalton et al., "Synthesis and Processing of Improved Organic Second-Order Nonlinear Optical Materials for Applications in Photonics," *Chemistry of Materials*, Vol. 7, No. 6, pp. 1060-1081 (1995). In contrast to inorganic materials, these organic materials can be systematically modified to improve electro-optic activity by the design and development of new organic materials and by the development of improved processing methods. See L. Dalton et al., "The Role of London Forces in Defining Noncentrosymmetric Order of High Dipole Moment-High Hyperpolarizability Chromophores in Electrically Poled Polymeric Films," *Proceedings of the National Academy of Sciences USA*, Vol. 94, pp. 4842-4847 (1997).

For an organic nonlinear optical material to be suitable for electro-optic applications, the material should have a large molecular optical nonlinearity, referred to as hyperpolarizability ($\beta$), and a large dipole moment ($\mu$). A commonly figure of merit used to compare materials is the value $\mu\beta$. See Dalton et al. (1997). Organic materials having $\mu\beta$ values greater than about $15,000\times10^{-48}$ esu that also satisfy the desired thermal and chemical stability and low optical loss at operating wavelengths have only recently been prepared. See Dalton et al., "New Class of High Hyperpolarizability Organic Chromophores and Process for Synthesizing the Same," WO 00/09613. However, materials characterized as having such large $\mu\beta$ values suffer from large intermolecular electrostatic interactions that lead to intermolecular aggregation resulting in light scattering and unacceptably high values of optical loss. See Dalton et al. (1997). A chromophore's optical nonlinearity ($\mu\beta$) can be measured as described in Dalton et al., "Importance of Intermolecular Interactions in the Nonlinear Optical Properties of Poled Polymers," *Applied Physics Letters*, Vol. 76, No. 11, pp. 1368-1370 (2000). A chromophore's electro-optic coefficient ($r_{33}$) can be measured in a polymer matrix using attenuated total reflection (ATR) technique at telecommunication wavelengths of 1.3 or 1.55 µm. A representative method for measuring the electro-optic coefficient is described in Dalton et al., "Importance of Intermolecular Interactions in the Nonlinear Optical Properties of Poled Polymers," *Applied Physics Letters*, Vol. 76, No. 11, pp. 1368-1370 (2000).

Many molecules can be prepared having high hyperpolarizability values, however their utility in electro-optic devices is often diminished by the inability to incorporate these molecules into a host material with sufficient noncentrosymmetric molecular alignment to provide a device with acceptable electro-optic activity. Molecules with high hyperpolarizability typically exhibit strong dipole-dipole interactions in solution or other host material that makes it difficult, to achieve a high degree of noncentrosymmetric order without minimizing undesirable spatially anisotropic intermolecular electrostatic interactions.

Chromophore performance is dependent on chromophore shape. See Dalton et al., "Low (Sub-1-Volt) Halfwave Voltage Polymeric Electro-optic Modulators Achieved by Controlling Chromophore Shape," *Science*, Vol. 288, pp. 119-122 (2000).

Chemical, thermal, and photochemical stabilities are imparted to the chromophores through their chemical structure and substituent choice. For example, in certain embodiments, the chromophore's active hydrogens are substituted with groups (e.g., alkyl, fluorine) to impart increased stability to the chromophore.

Thus, the effectiveness of organic nonlinear optical materials having high hyperpolarizability and large dipole moments can be limited by the tendency of these materials to aggregate when processed into electro-optic devices. The result is a loss of optical nonlinearity. Accordingly, improved nonlinear optically active materials having large hyperpolarizabilities and large dipole moments and that, when employed in electro-optic devices, exhibit large electro-optic coefficients may be advantageous for many applications.

For the fabrication of practical electro-optical (E-O) devices, critical material requirements, such as large E-O coefficients, high stability (thermal, chemical, photochemical, and mechanical), and low optical loss, need to be simultaneously optimized. In the past decade, a large number of highly active nonlinear optical (NLO) chromophores have been synthesized, and some of these exhibit very large macroscopic optical nonlinearities in high electric field poled guest/host polymers. To maintain a stable dipole alignment, it is a common practice to utilize either high glass transition temperature ($T_g$) polymers with NLO chromophores as side chains or crosslinkable polymers with NLO chromophores that could be locked in the polymer network. However, it is difficult to achieve both large macroscopic nonlinearities and good dipole alignment stability in the same system. This is due to strong intermolecular electrostatic interactions among high dipole moment chromophores and high-temperature aromatic-containing polymers, such as polyimides and polyquinolines that tend to form aggregates. The large void-containing dendritic structures may provide an attractive solution to this critical issue because the dendrons can effectively decrease the interactions among chromophores due to the steric effect. Furthermore, these materials are monodisperse, well-defined, and easily purifiable compared to polymers that are made by the conventional synthetic approaches.

SUMMARY OF THE INVENTION

The present invention provides nonlinear optically active compounds, macrostructures that include nonlinear optically active components, and devices including the macrostructures.

In one aspect, the invention provides nonlinear optically active compounds. The compounds include dendrimers having two or more nonlinear optically active components (i.e., chromophores). In these dendrimers, the nonlinear optically active component or chromophore is embedded within a molecular structure that effectively insulates the chromophore dipole from interaction with other such dipoles. In one embodiment, the dendrimer is a crosslinkable dendrimer.

In another aspect of the invention, macrostructures that include the compounds or nonlinear optically active components are provided. In one embodiment, the nonlinear optically active components are covalently coupled within the macrostructure.

In a further aspect, the invention provides devices that include the nonlinear optically active compounds and devices that include the macrostructures.

In other aspects, methods for making the nonlinear optically active compounds, the macrostructures that include nonlinear optically active components, and the devices including the compounds and macrostructures are provided.

In one embodiment, the invention provides a crosslinkable nonlinear optically (NLO) dendrimer exhibiting very large optical nonlinearity and excellent thermal stability. This dendrimer is constructed through a double-end functionalization of a phenyl-tetracyanobutadienyl (Ph-TCBD) thiophene-stilbene-based NLO chromophore as the center core and crosslinkable trifluorovinyl ether-containing dendrons at the dendrimer periphery. Spatial isolation of the nonlinear optical component (i.e., chromophore) from the dendrimer shell decreases chromophore-chromophore electrostatic interactions, and thus enhances macroscopic optical nonlinearity because electrostatic interactions among chromophores play a critical role in defining the maximum macroscopic optical nonlinearity that can be achieved for a given chromophore. In addition, because of the dendrimer's relatively high molecular weight, the dendrimer can be directly spin-coated without the usual prepolymerization process needed to build up viscosity. The dendrimer is a multi-chromophoric dendrimer having a chromophore loading density of 33 w/w %. The dendrimer also possesses excellent alignment stability and mechanical properties, which are obtained through the sequential hardening/crosslinking reactions during the high-temperature electric-field poling process. Very large E-O coefficient ($r_{33}$=60 pm/V at 1.55 µm), and long-term alignment stability (retaining >90% of its original $r_{33}$ value at 85° C. for more than 1000 h) were achieved for the poled dendrimer.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A is an illustration of a convergent synthesis for a representative multi-chromophoric dendrimer of the invention;

FIG. 2B is an illustration of a divergent synthesis for a representative multi-chromophoric dendrimer of the invention;

FIG. 2C is an illustration of a hybrid synthesis for a representative multi-chromophoric dendrimer of the invention;

DETAILED DESCRIPTION OF THE PREFERRED EMBODIMENT

Figure 1:
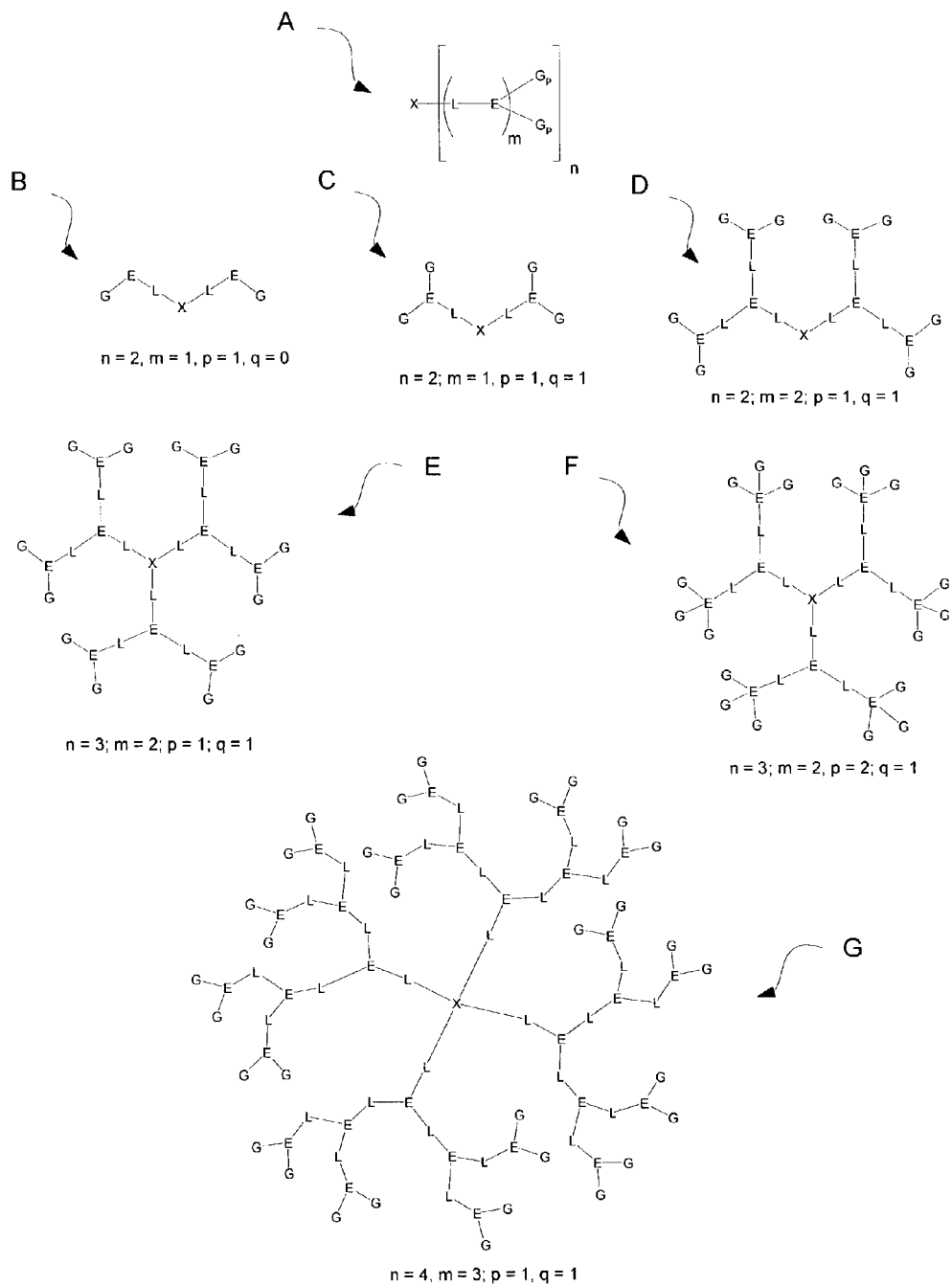
FIG. 1A is a general chemical structure for the multi-chromophoric dendrimers of the invention.
FIGS. 1B-1G are chemical structures for representative multi-chromophoric dendrimers of the invention.
Figure 3:
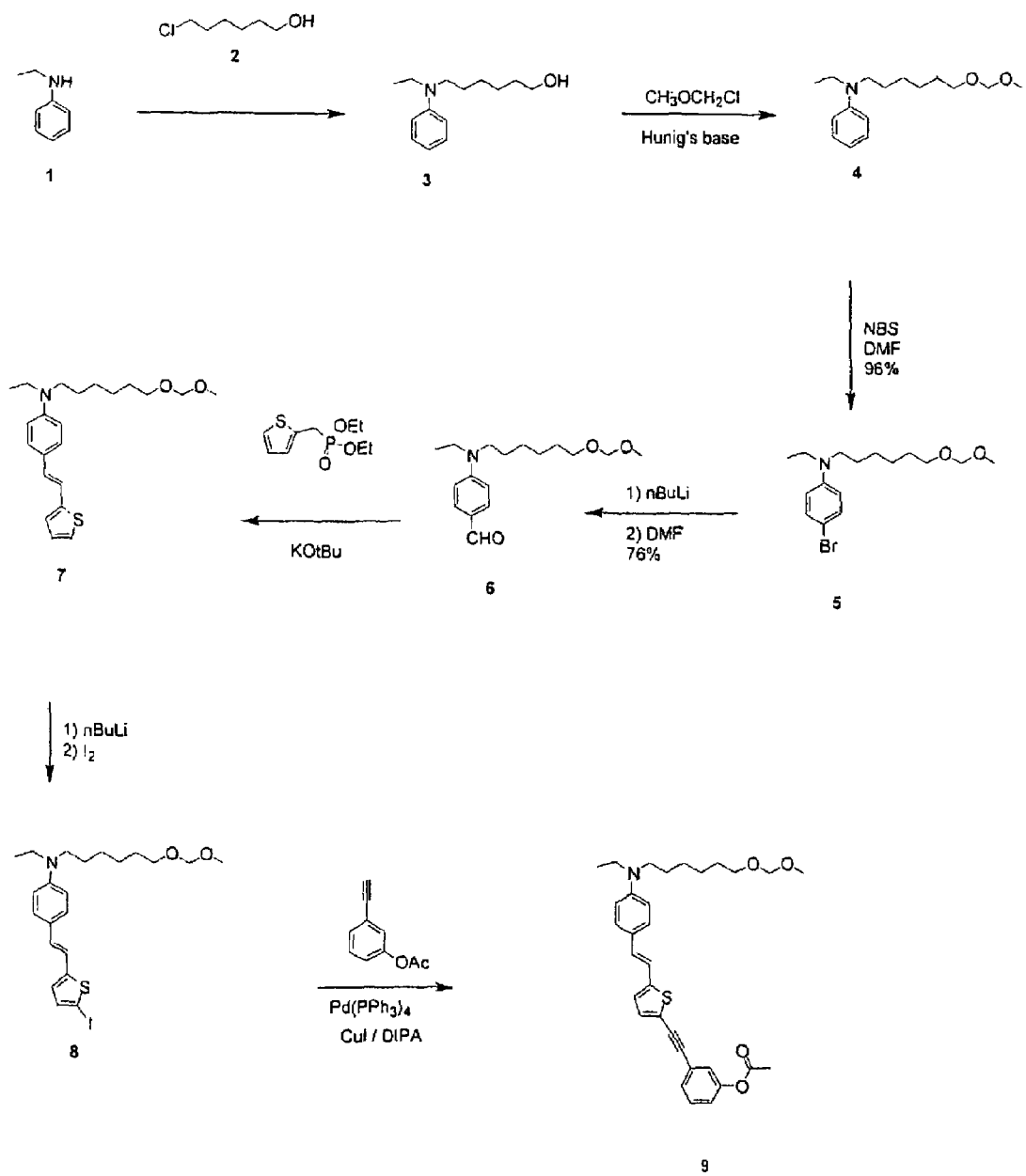
FIGS. 3-6 are a schematic illustration of the synthesis of a representative multi-chromophoric dendrimer of the invention.
Figure 4:
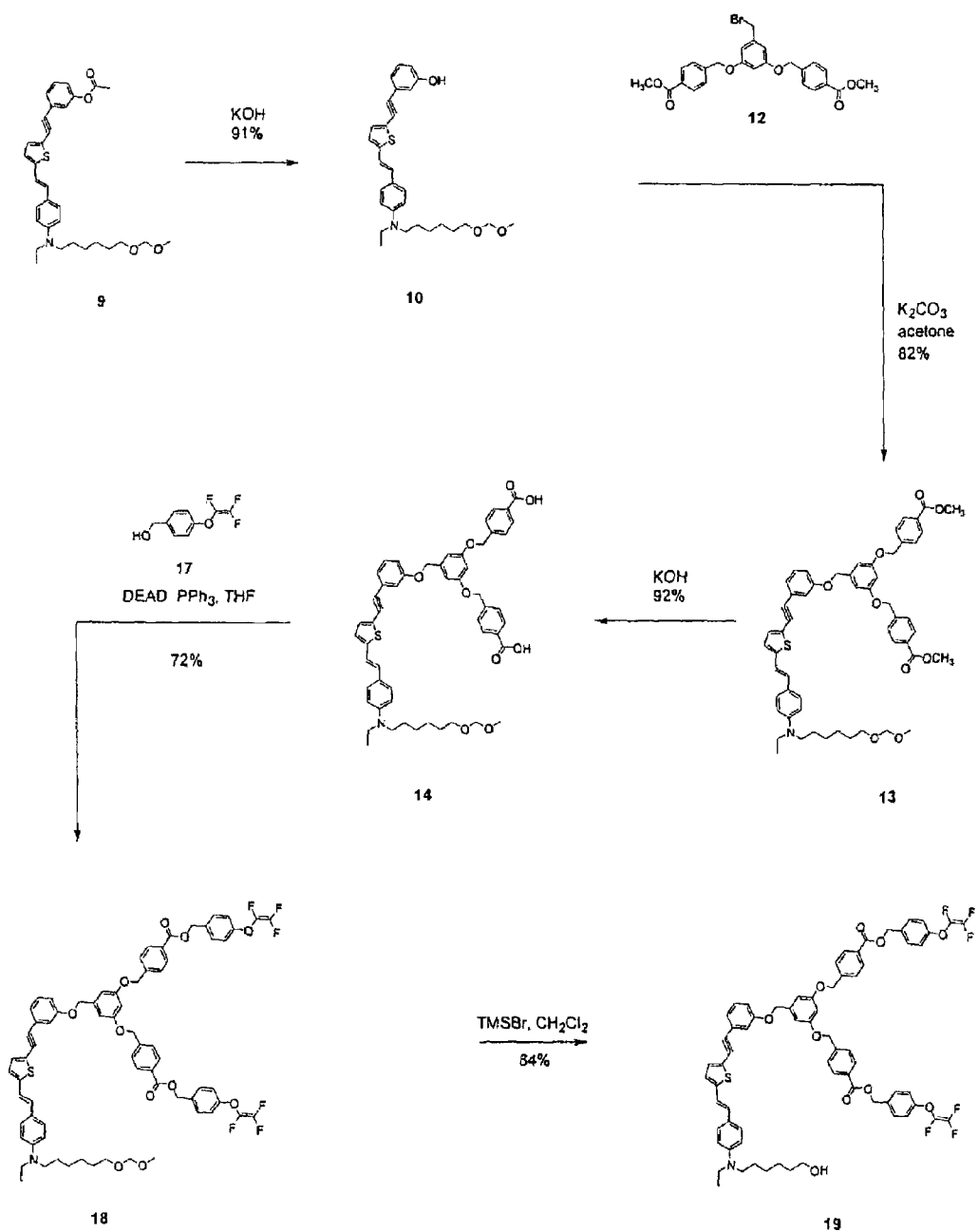
Figure 5:
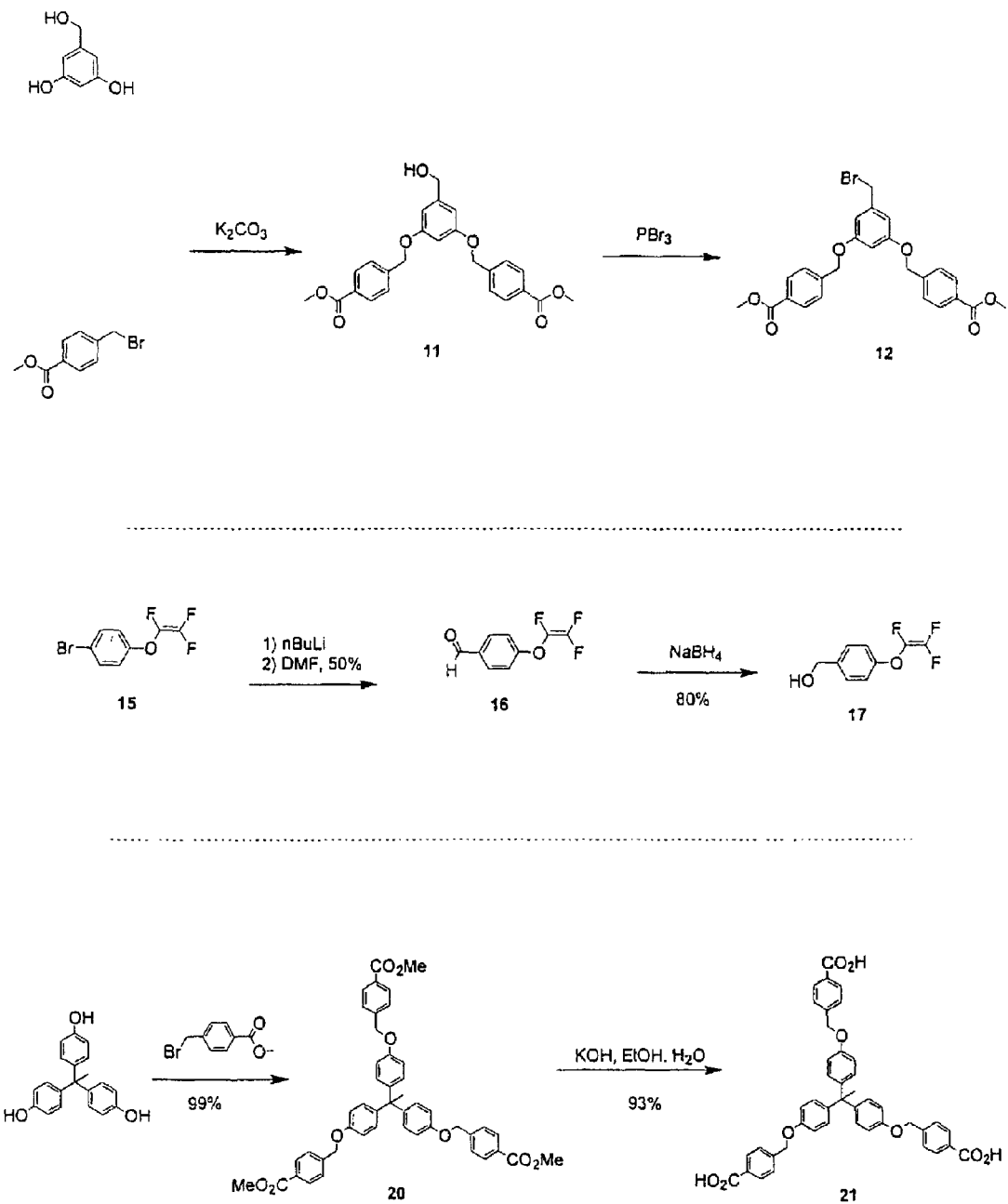
Figure 6:
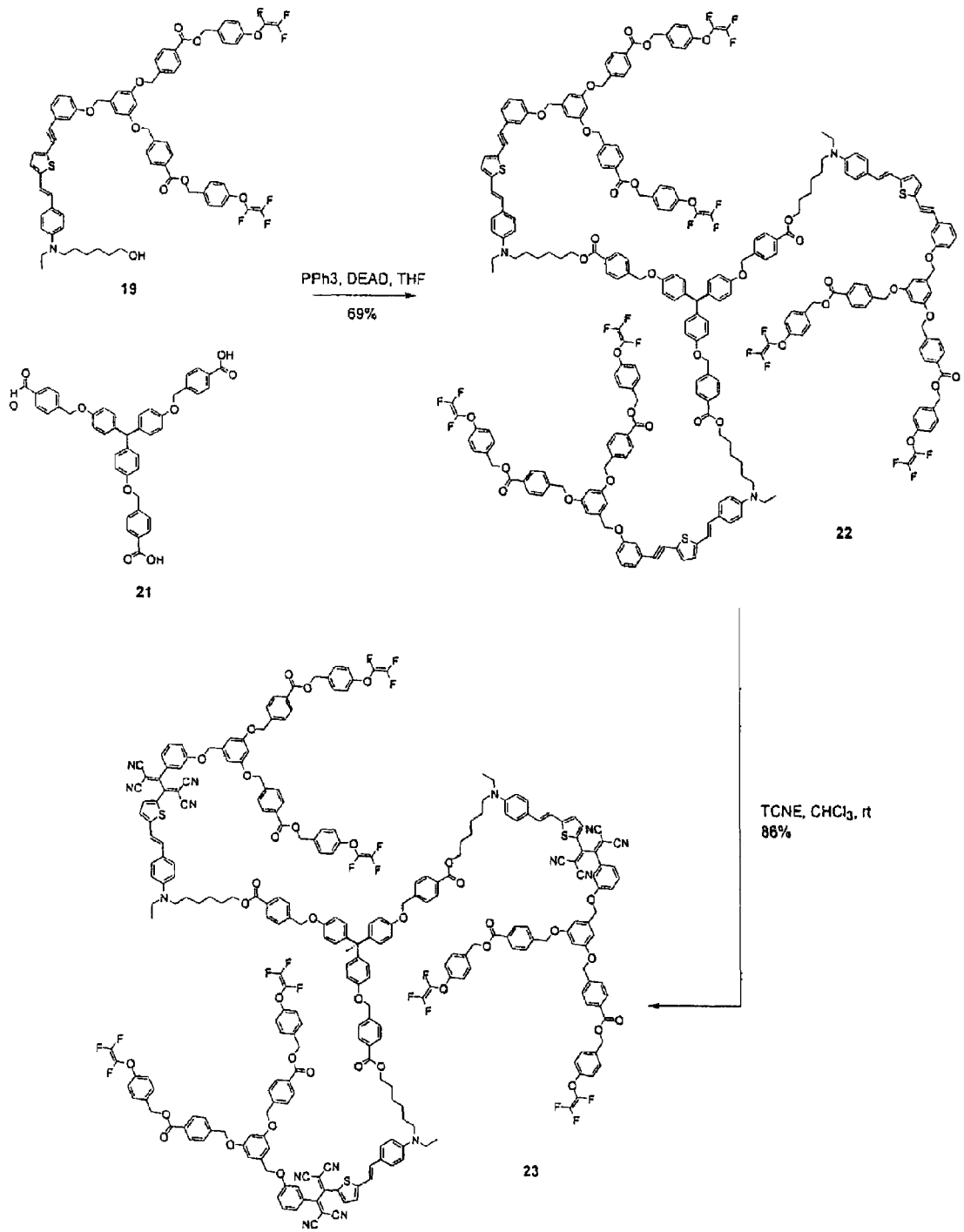
Figure 7:
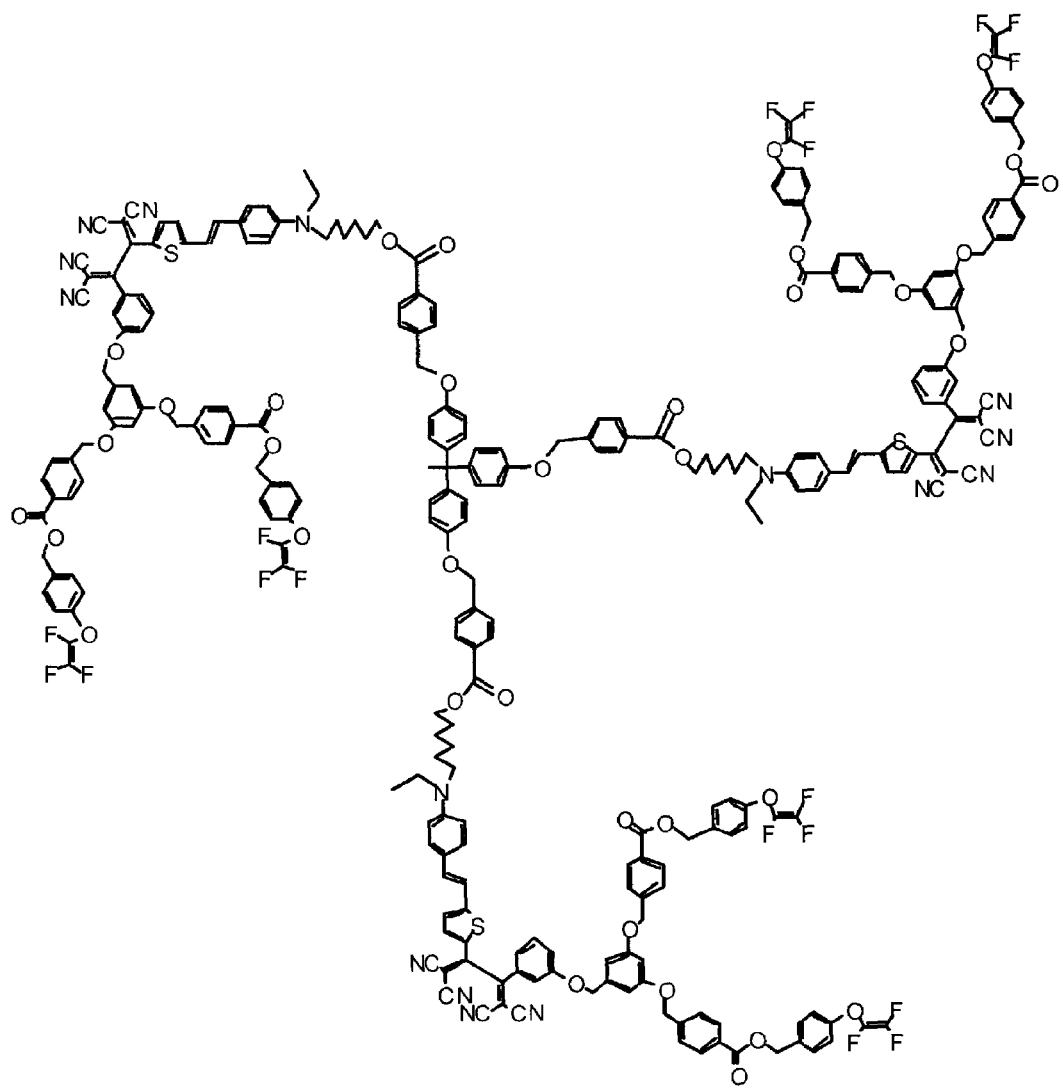
FIG. 7 is the chemical structure of a representative multi-chromophoric dendrimer of the invention.

The present invention provides nonlinear optically active compounds, macrostructures that include nonlinear optically active components, and devices including the compounds and macrostructures.

In one aspect, the invention provides nonlinear optically active compounds. The compounds include dendrimers having two or more nonlinear optically active components (i.e., chromophores). In these dendrimers, the nonlinear optically active component or chromophore is embedded within a molecular structure that effectively insulates the chromophore dipole from interaction with other such dipoles. Through the use of substitution and control of dendrimer shape, high electro-optic coefficients ware achieved when these dendrimers are incorporated into electro-optic devices. In one embodiment, the dendrimer is a crosslinkable dendrimer. As used herein, the term "multi-chromophoric dendrimer" refers to a dendrimer that includes two or more chromophores (i.e., nonlinear optically active components). The syntheses of two representative multi-chromophoric dendrimers are described in Examples 1 and 2. Representative multi-chromophoric dendrimers are illustrated in FIGS. 1, 2, 7-10, and 18. The synthesis of crosslinkable nonlinear optically active compounds and their related macrostructures are described in Example 3 and illustrated in FIG. 16.

In another aspect of the invention, macrostructures that includes the compounds or nonlinear optically active components are provided. In one embodiment, the nonlinear optically active components are covalently coupled within the macrostructure. Representative macrostructures of the invention can be prepared from dendrimers that include two or more nonlinear optically active components and that include reactive chemical groups at the dendrimer's periphery rendering the dendrimer crosslinkable. Other representative macrostructures of the invention can be prepared from nonlinear optically active compounds that include reactive chemical groups rendering the compound crosslinkable.

In a further aspect, the invention provides devices that include the nonlinear optically active compounds and devices that include the macrostructures.

Other aspects of the invention relate to methods for making the nonlinear optically active compounds, methods for making the macrostructures that include nonlinear optically active components, and methods for making the devices including the compounds and macrostructures.

To better understand the present invention, the following definitions are provided. In general, all technical and scientific terms used herein have the same meaning as commonly understood to one of skill in the art to which this invention belongs, unless clearly indicated otherwise. When an element is cited, all of the element's isotopes are implicitly included (e.g., "hydrogen" stands for hydrogen, deuterium, and tritium). If an isotope is identified explicitly, it is represented by a superscript of the atomic number immediately preceding the symbol (i.e., deuterium is "$^2$H" not "D"). For clarification, listed below are definitions for certain terms used herein to describe embodiments of the present invention. These definitions apply to the terms as they are used throughout this specification, unless otherwise clearly indicated.

As used herein the singular forms "a", "and", and "the" include plural referents unless the context clearly dictates otherwise. For example, "a group" refers to one or more of such groups, while "a chromophore" includes a particular chromophore as well as other family members and equivalents thereof as known to those skilled in the art.

Both substituent groups and molecular moieties are sometimes represented herein with symbols (e.g., R, $R^1$, $\pi$, $\pi^1$, $\pi^2$, D, and A). When the phrase "independently at each occurrence" refers to a symbol, that symbol may represent different actual substituent groups or molecular moieties every time the symbol appears in a formula. For example, the structure below, when described by "wherein R independently at each occurrence is methyl or hydrogen", would correspond to phenol as wells as several methyl substituted phenols including 2-methyl phenol, 3-methyl phenol, 3,4-dimethylphenol, and 2,4,6-trimethylphenol, etc.

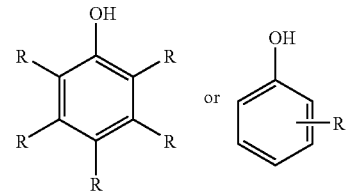

"Chromophore" refers to any molecule, aggregate of molecules, or macromolecular structure that absorbs light. Thus, a chromophore can mean a single molecule that absorbs light, an aggregate or macromolecule containing only one absorbing molecule, or an aggregate or macromolecule containing more than one absorbing molecule.

"Electro-optic" (E-O) pertains to altering optical properties of a material by the occurrence of an electric field.

"Electronic" when used to refer to chemical structures and molecules, as opposed to electro-optic devices and components, pertains to electrons in a molecule or on an atom.

"Electric" pertains to electricity and electrical phenomena arising from applied voltages.

"Temporal stability" refers to long-term retention of a particular property. Temporal stability may be affected by any factor that modifies changes in either intermolecular order or intramolecular chemical structure.

A "π-bridge" or "conjugated bridge" (represented in chemical structures by "$\pi$" or "$\pi^n$" where n is an integer) is comprised of an atom or group of atoms through which electrons can be delocalized from an electron donor (defined below) to an electron acceptor (defined below) through the orbitals of atoms in the bridge. Preferably, the orbitals will be p-orbitals on multiply bonded carbon atoms such as those found in alkenes, alkynes, neutral or charged aromatic rings, and neutral or charged heteroaromatic ring systems. Additionally, the orbitals can be p-orbitals on multiply bonded atoms such as boron or nitrogen or organometallic orbitals. The atoms of the bridge that contain the orbitals through which the electrons are delocalized are referred to here as the "critical atoms." The number of critical atoms in a bridge can be a number from 1 to about 30. The critical atoms can also be substituted further with the following: "alkyl" as defined below, "aryl" as defined below, or "heteroalkyl" as defined below. One or more atoms, with the exception of hydrogen, on alkyl, aryl, or heteroalkyl substituents of critical atoms in the bridge may be bonded to atoms in other alkyl, aryl, or heteroalkyl substituents to form one or more rings.

A "donor" (represented by "D") is an atom or group of atoms with low electron affinity relative to an acceptor (defined below) such that, when the donor is conjugated to an acceptor through a π bridge, electron density is transferred from the donor to the acceptor.

An "acceptor" (represented by "A") is an atom or group of atoms with high electron affinity relative to a donor such that, when the acceptor is conjugated to a donor through a π bridge, electron density is transferred from the acceptor to the donor.

Representative donors, acceptors, and π-bridges known to those skilled in the art are described in U.S. Pat. Nos. 6,067,186; 6,090,332; 5,708,178; and 5,290,630.

"Nonlinear" when used in the context of optical phenomenon pertains to second order effects. Such second order, or non-linear, effects typically arise from a "push-pull" chromophore, i.e., a chromophore with the general structure D-π-A.

"Donor coupling" or "π-bridge and/or donor coupling" describe the synthetic chemical step or steps known to those skilled in the art of covalently attaching a chemical group containing a donor to a selected chemical structure. The step maybe divided into multiple steps, wherein the first step covalently attaches a π-bridge that is also reactive and the second step covalently attaches a donor group. Typically, the coupling involves either reacting a π-bridge or donor group containing a carbonyl with a selected chemical structure containing at least one acidic proton or reacting a π-bridge or donor group containing at least one acid proton with a selected chemical structure containing a reactive carbonyl group.

"Acceptor coupling" or "π-bridge and/or acceptor coupling" is the synthetic chemical step or steps known to those skilled in the art of covalently attaching a chemical group containing an acceptor to a selected chemical structure. The step maybe divided into multiple steps, wherein the first step covalently attaches a π-bridge that is also reactive and the second step covalently attaches an acceptor group. Typically, the coupling involves either reacting a π-bridge or acceptor group containing a carbonyl with a selected chemical structure containing at least one acidic proton or reacting a π-bridge or acceptor group containing at least one acid proton with a selected chemical structure containing a reactive carbonyl group.

"Dendron" is a branched substituent that has regularly repeating subunits. A dendrimer is a macromolecular structure that contains a core surrounded by one or more dendrons. Often in the art, the terms dendron and dendrimer are used interchangeably.

As used herein, "R" or "R$_n$'" where n is an integer refers to a substituent on an atom. Unless otherwise specifically assigned, —R represents any single atom or any one of the substituent groups defined below. When there is more than one —R in a molecule, the "—R" may independently at each occurrence refer to a single atom or any one of the substituent groups defined below.

The following definitions apply to substituent groups. A given substituent group can have a total number of carbons atoms ranging from 1 to about 200.

"Alkyl" is a saturated or unsaturated, straight or branched, cyclic or multicyclic aliphatic (i.e., non-aromatic) hydrocarbon group containing from 1 to about 30 carbons. Independently the hydrocarbon group, in various embodiments: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH═$CH_2$ (ethenyl) and —C≡CH (ethynyl)) and $C_3$alkyl (i.e., —$CH_2CH_2CH_3$ (n-propyl), —CH($CH_3$)$_2$ (1-propyl), —CH═CH—$CH_3$ (1-propenyl), —C≡C—$CH_3$ (1-propynyl), —$CH_2$—CH═$CH_2$ (2-propenyl), —$CH_2$—C≡CH (2-propynyl), —C($CH_3$)═$CH_2$ (1-methylethenyl), —CH($CH_2$)$_2$ (cyclopropyl), and adamantly. The term "alkyl" also includes groups where at least one of the hydrogens of the hydrocarbon group is substituted with at least one of the following: alkyl; "aryl" as defined below; or "heteroalkyl" as defined below. One or more of the atoms in an alkyl group, with the exception of hydrogen, can be bonded to one or more of the atoms in an adjacent alkyl group, aryl group (aryl as defined below), or heteroalkyl group (heteroalkyl as defined below) to form one or more ring.

"Aryl" is a monocyclic or polycyclic aromatic ring system or a hetereoaromatic ring system containing from 3 to about 30 carbons. The ring system may be monocyclic fused polycyclic (e.g., bicyclic, tricyclic, etc.). Preferred heteroatoms are nitrogen, oxygen, sulfur, and boron. In various embodiments, the monocyclic aryl ring is C5-C10, or C5-C7, or C5-C6, where these carbon numbers refer to the number of carbon atoms that form the ring system. A C6 ring system, i.e., a phenyl ring, is a preferred aryl group. A C4-S ring system (i.e., a thiophene) is another preferred aryl group. In various embodiments, the polycyclic ring is a bicyclic aryl group, where preferred bicyclic aryl groups are C8-C12, or C9-C10. A naphthyl ring, which has 10 carbon atoms, is a preferred polycyclic aryl group. The term "aryl" also includes groups where at least one of the hydrogens of the aromatic or heteroaromatic ring system is substituted further with at least one of the following: alkyl; halogen; or hetereoalkyl (as defined below). One or more of the atoms in an aryl group, with the exception of hydrogen, can be bonded to one or more of the atoms in an adjacent alkyl group, aryl group, or heteroalkyl group (heteroalkyl as defined below) to form one or more rings.

"Heteroalkyl" is an alkyl group (as defined herein) wherein at least one of the carbon atoms or hydrogen atoms is replaced with a heteroatom, with the proviso that at least one carbon atom must remain in the heteroalkyl group after the replacement of carbon or hydrogen with a heteroatom. Preferred heteroatoms are nitrogen, oxygen, sulfur, silicon, and halogen. A heteroatom may, but typically does not, have the same number of valence sites as the carbon or hydrogen atom it replaces. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. Examples of heteroalkyls derived from alkyls by replacement of carbon or hydrogen with heteroatoms is shown immediately below. Exemplary heteroalkyl groups are methoxy (—OCH$_3$), amines (—CH$_2$NH$_2$), nitriles (—CN), carboxylic acids (—CO$_2$H), other functional groups, and dendrons. The term "heteroalkyl" also includes groups where at least one of the hydrogens of carbon or a heteroatom of the heteroalkyl may be substituted with at least one of the following: alkyl; aryl; and heteroalkyl. One or more of the atoms in a heteroalkyl group, with the exception of hydrogen, can be bonded to one or more of the atoms in an adjacent alkyl group, aryl group, or heteroalkyl group to form one or more rings.

1999, 99, 1665-1688; (3) (aryl) —C$_6$H$_5$ (phenyl), p-, o-, and/or m-substituted phenyl (with substituents independently selected from —CH$_3$, -i-Pr, -n-Bu, -t-Bu, -i-Bu, —X$_{(0-1)}$(CH$_2$)$_{(0-12)}$(CF$_2$)$_{(0-12)}$(CH$_2$)$_{(0-12)}$CH$_p$Z$_q$ (where X includes —O, —S, —CO$_2$— (ester), Z=halogen, p=0-3, q=0-3, and p+q=3) and branched isomers thereof, —X$_{(0-1)}$(CH$_2$)$_{(0-12)}$(CF$_2$)$_{(0-12)}$(CH$_2$)$_{(0-12)}$Z (where X includes —O, —S, —CO$_2$— (ester), Z includes —OH, —NH$_2$, —CO$_2$H and esters and amides thereof, -TFVE, —COCl, and —NCO) and branched isomers thereof, —Si(CH$_3$)$_3$ (TMS), —Si(CH$_3$)$_2$(t-

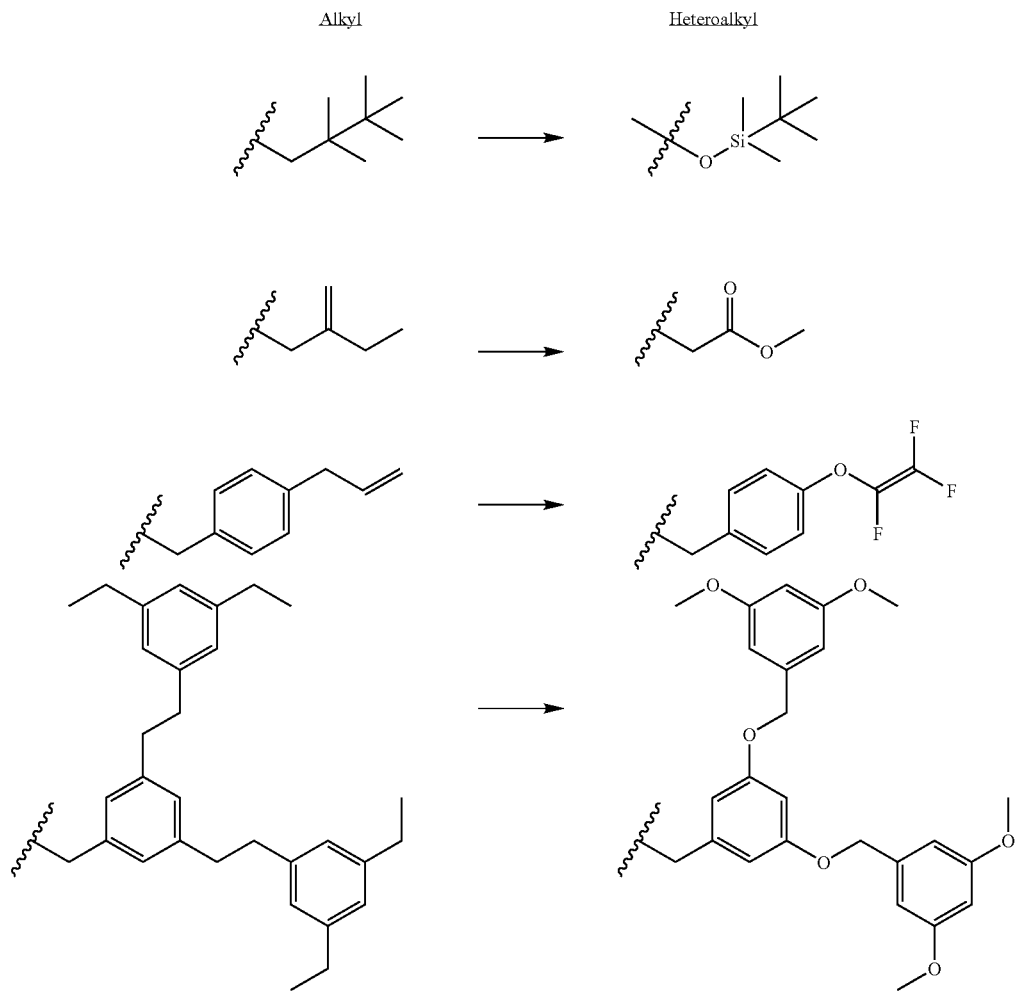

Bu) (TBDMS), —CH$_2$CH=CH$_2$ (allyl), and TFVE) and dendrons as illustrated in the dendrimers discussed in Bosman et al., *Chem. Rev.*, Vol. 99, p. 1665 (1999) or U.S. Pat. No. 5,041,516.

The multi-chromophoric dendrimers and related macrostructures described herein are characterized by exceptionally large electro-optic coefficients and very good temporal stability under accelerated aging at 85° C. for 1000 h. The large electro-optic coefficient of the multi-chromophoric dendrimers is about twice the value of that for either host guest systems employing the same chromophore as in the multi-chromophoric dendrimer or single chromophore dendrimers incorporating a higher μβ chromophore than are in the multi-chromophoric dendrimers.

The substituent list that follows is not meant to limit the scope of the definitions above or the inventions described below, but rather merely contains examples of substituents within the definitions above: (1) (alkyl) —CH$_3$, -i-Pr, -n-Bu, -t-Bu, -i-Bu, —CH$_2$CH=CH$_2$ (allyl) —CH$_2$C$_6$H$_5$ (benzyl); (2) (heteroalkyl) —X$_{(0-1)}$(CH$_2$)$_{(0-12)}$(CF$_2$)$_{(0-12)}$(CH$_2$)$_{(0-12)}$CH$_p$Z$_q$ (where X includes —O, —S, —CO$_2$— (ester), Z=halogen, p=0-3, q=0-3, and p+q=3) and branched isomers thereof, —X$_{(0-1)}$(CH$_2$)$_{(0-12)}$(CF$_2$)$_{(0-12)}$(CH$_2$)$_{(0-12)}$Z (where X includes —O, —S, —CO$_2$— (ester), Z includes —OH, —NH$_2$, —CO$_2$H and esters and amides thereof, —COCl, and —NCO) and branched isomers thereof, —OCFCF$_2$ (TFVE), —Si(CH$_3$)$_3$ (TMS), —Si(CH$_3$)$_2$(t-Bu) (TBDMS), —Si(C$_6$H$_5$) (TPS), —Si(C$_6$F$_5$)$_3$, and dendrons such as illustrated in the dendrimers discussed in Bosman et al., *Chem. Rev.*

The multi-chromophoric dendrimers can be represented by the general structure:

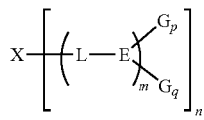

where n=2 to about 12; m=1 to about 8; p=1 to about 6; q=0 to about 6; X is an alkyl, hetereoalkyl, or aryl core that is linked to a non-linear optically active D-π-A chromophore E by a linker L; E at any occurrence can be structurally different from any other E in the dendrimer; L is independently at each occurrence alkyl, hetereoalkyl, or aryl; L is covalently bound to at least one alkyl, heteroalkyl, or aryl substituent on any one of D, π, or A of E; and G is independently at each occurrence a chemical group that is reactive under selected conditions.

For clarification, the letter m corresponds to the dendron "generation" as the term is commonly used in the art, see *Chem. Rev.*, Vol. 99, p. 1665 (1999) and U.S. Pat. No. 5,041,516. For example, m=2 corresponds to a second generation dendron, m=3 corresponds to a third generation dendron, m=4 corresponds to a fourth generation dendron, and etc. The letter n corresponds to how many dendrons are covalently attached to the core. The letters p and q represent the number of independent chemical groups, which are reactive at selected conditions, that are attached to each peripheral chromophore. The sum of p and q (p+q) is ultimately the important number, i.e., three reactive chemical groups per peripheral chromophore could be represented by p=3 and n=0; p=2 and n=1; p=1 and n=2; or p=0 and n=3. The number of selectively reactive chemical groups per dendrimer then would be the product of n and the product of m and the sum of p and q, i.e., the total number of selectively reactive chemical groups=n (m(p+q)). Some representative examples of multi-chromophoric dendrimers and the corresponding n, m, p, and q values are shown in FIGS. 1A-1G.

Core X and linker L provide some isolation between the chromophores in the dendrimer. The isolation is meant, in some cases, to decrease the dipole-dipole intermolecular interactions that occur when the chromophores can closely approach each other. The linker L can be independently at each occurrence covalently attached to chromophore E through at least one substituent any one of D, π, or A. The selectively reactive groups G are linked to chromophores by an alkyl, heteroalkyl, or aryl linker that is independent and not particularly related to any of the linkers L. In general, the G group is chosen to effect polymerization or crosslinking of the thin films comprising the dendrimer. Thus, G is ultimately capable of reacting with either a G group on another dendrimer or a chemically reactive group, which is either identical to or different than G, attached to an additive of the thin film. In many cases, the dendrimer can be spin coated onto a substrate and directly crosslinked by one of many conditions including heat and irradiation.

The dendrimers can be synthesized by convergent, divergent, or hybrid approaches such as illustrated in FIGS. 2A-2C, respectively. In the convergent approach, the eventual periphery is synthesized first (G+E-L) followed by the synthesis of the second generation dendron and finally coupling to the core to produce an n=3; m=2; p=1; and q=1 dendrimer. In the divergent approach, the core is coupled to a linker chromophore pair (E-L) and then product dendrimer is again coupled to an E-L pair followed by coupling to the chemically reactive group G. An example of a hybrid approach would be divergently synthesizing the first generation dendrimer followed by coupling to a convergently synthesized $G_n$-E-L periphery. Thus, using three different approaches, three different dendrimers of the n=3; m=2; p=1; and q=1 motif could be synthesized. One important aspect common to all approaches is that a chromophore or linker in any one generation of the dendrimer can be varied independently of any chromophore or linker in another generation of the dendrimer. Such synthetic flexibility in the construction of the dendrimer can be useful if, for example, one wants to use a less expensive chromophore in the periphery, a more or less nonlinear chromophore in the in the initial generations, or a longer linker in either the peripheral or near the core.

There are numerous functional groups that can be used in the synthesis of the novel dendrimers. Referring to FIG. 2A, in the convergent approach E can have substituent hydroxy group that can be reacted with an acid chloride functional group of G, L can have a "protected" functional group such as an ester that can be converted to a carboxylic acid and coupled to hydroxy or amine functionalities on the next E-L pair to give the second generation dendron, and finally another functional group such as a hydroxy on $L^1$ can be coupled to an acid functionality on the core X. There are many reactive functional group pairs that can be used for couplings at various stages of the dendrimer synthesis including but not limited to alcohols and acid derivatives, amines and acid derivatives, alkyl halides and nucleophiles, aryl halides and terminal acetylenes, aryl halides and alkenes, aryl halides and organotins, aryl halides and boronic acids, isocyanates and nucleophiles, and etc.

Representative dendrimer 23 was prepared as described in Example 1. Briefly, the dendrimer was synthesized by the Mitsunobu condensation between the carboxyl groups on the three branches of the desirable core molecule and the hydroxy-containing chromophore precursor that has crosslinkable trifluorovinyl ether on the dendrons. Then, the intermediate was reacted with tetracyanoethylene (TCNE) to activate the Ph-TCBD electron acceptor. Synthetic schemes for the dendrimer's preparation are illustrated in FIGS. 3-6. The purity and structure of the dendrimer were fully characterized by gel permeation chromatography (GPC), matrix-assisted laser desorption/ionization time-of-flight (MALDI-TOF) mass spectrometry, and $^1$H and $^{19}$F NMR spectroscopy. The GPC trace shows a single, sharp, and symmetrical peak that indicates a single component in the material. This result was confirmed by the MALDI-TOF mass spectrometry that a peak corresponding to the mass unit of the NLO dendrimer with the formula of $C_{269}H_{207}F_{18}N_{15}O_{36}S_3$ was obtained. All of the resonance peaks in the $^1$H NMR spectrum can be assigned to the protons of different moieties on the NLO dendrimer.

This dendrimer is soluble in chloroform, cyclopentanone, and THF. Pinhole free thin films can be processed directly from the dendrimer solution using cyclopentanone/mesitylene as the co-solvents. The UV/VIS spectrum of the dendrimer film exhibits a strong absorption maximum at 655 nm ascribed to the π-π* charge-transfer band of the NLO chromophore. The NLO dendrimer also possesses very low birefringence ($n_{TE}$=1.6419, $n_{TM}$=1.6408) at 1.55 μm due to its three-dimensional (3-D) isotropic structure.

Thermal analysis of this dendrimer by differential scanning calorimetry showed an endothermic melting peak at 73° C. and an exothermic transition above 140° C., at which temperature the peripheral trifluorovinyl ether groups were polymerized and crosslinked. For E-O measurements, the solution of the dendrimer in mesitylene/cyclopentanone (22 w/w % solution, filtered through a 0.2 µm syringe filter) was spin-coated onto an indium tin oxide (ITO) glass substrate. The film was heated under vacuum at 85° C. overnight to remove residual solvent. The dipole alignment was achieved by corona poling, and the $r_{33}$ value was measured using a simple reflection technique at 1.55 µm. After sequential heating (at 130° C. for 4 min, 150° C. for 5 min, 165° C. for 15 min, and 175° C. for 8 min) and poling (with 3.0 kV at 175° C. for 6 min and 3.2 kV at 190° C. for 10 min), a very large E-O coefficient ($r_{33}$=60 pm/V) was achieved for this dendrimer (crosslinkable dendrimer in Table 1). The resulting poled dendrimer also possessed excellent temporal stability that retained >90% of its original $r_{33}$ value at 85° C. for more than 1000 h. In comparison, E-O studies of a guest/host system in which a nondendron-modified similar structure chromophore (optimized loading level: 30 wt %) was formulated into a high-temperature polyquinoline (PQ-100) (guest/host polymer in Table 1). The glass transition temperature ($T_g$) of the resulting system is plasticized to approximately 165° C. After the same sequential heating and corona poling as that for the dendrimer, the guest/host system showed a much smaller E-O coefficient (less than 30 pm/V) and worse temporal stability (only retained <65% of its original $r_{33}$ value at 85° C. after 1000 h). In addition, the attempt to corona pole a non-trifluorovinyl ether functionalized dendrimer (non-crosslinkable dendrimer in Table 1) only showed a very fast decay of E-O signal (<10 pm/V) after the sample being poled and measured at room temperature. This is due to the intrinsic low $T_g$ (<50° C.) and very large free volume of the dendrimer (Table 1). On the basis of these results, the large $r_{33}$ of the poled dendrimer is largely due to the dendritic effect, which allows the NLO dendrimer to be efficiently aligned. On the other hand, the high temporal stability of the poled dendrimer mainly results from the efficient sequential crosslinking/poling process.

Thus, in one embodiment, the invention provides a highly efficient and thermally stable NLO dendrimer that includes a three-dimensional shape Ph-TCBD-containing chromophore that is double-end functionalized with the dendritic envelope and thermally cross-linkable trifluorovinyl ether periphery. The dendrimer exhibits a combination of large $r_{33}$ value of 60 pm/V at 1.55 µm and good temporal stability at 85° C.

TABLE 1

E-O Coefficients and Temporal Stability of Three NLO Material Systems.

| Material System | Electro-optic Coefficient ($r_{33}$, pm/V, at 1.55 µm) | Temporal Stability (%, after 1000 h at 85° C.) |
| --- | --- | --- |
| Crosslinkable dendrimer | 60 | >90 |
| Guest/host polymer | <30 | <65 |
| Non-crosslinkable dendrimer | <10 | fast decay |

Figure 8:
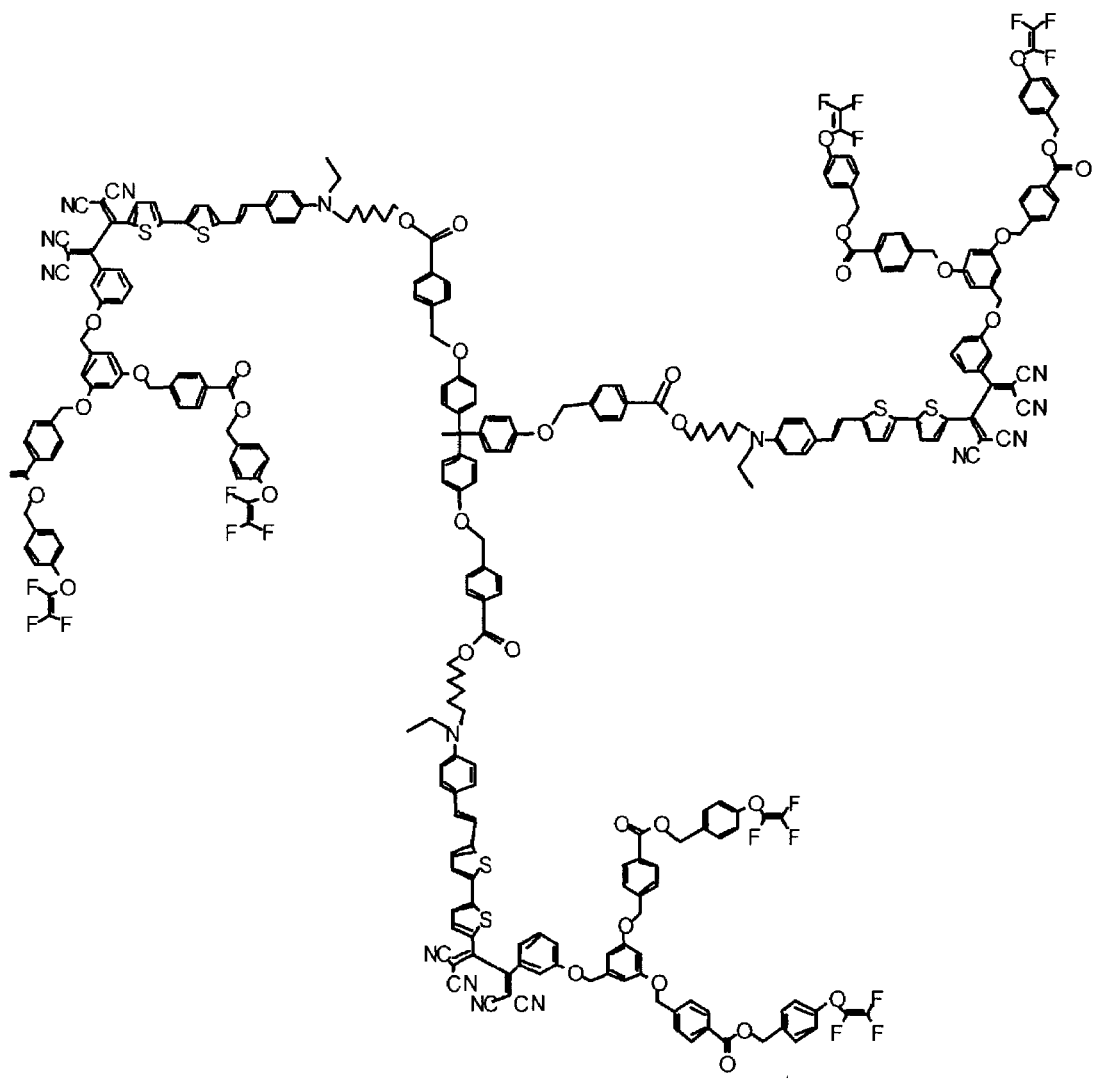
FIG. 8 is the chemical structure of a representative multi-chromophoric dendrimer of the invention.
Figure 9:
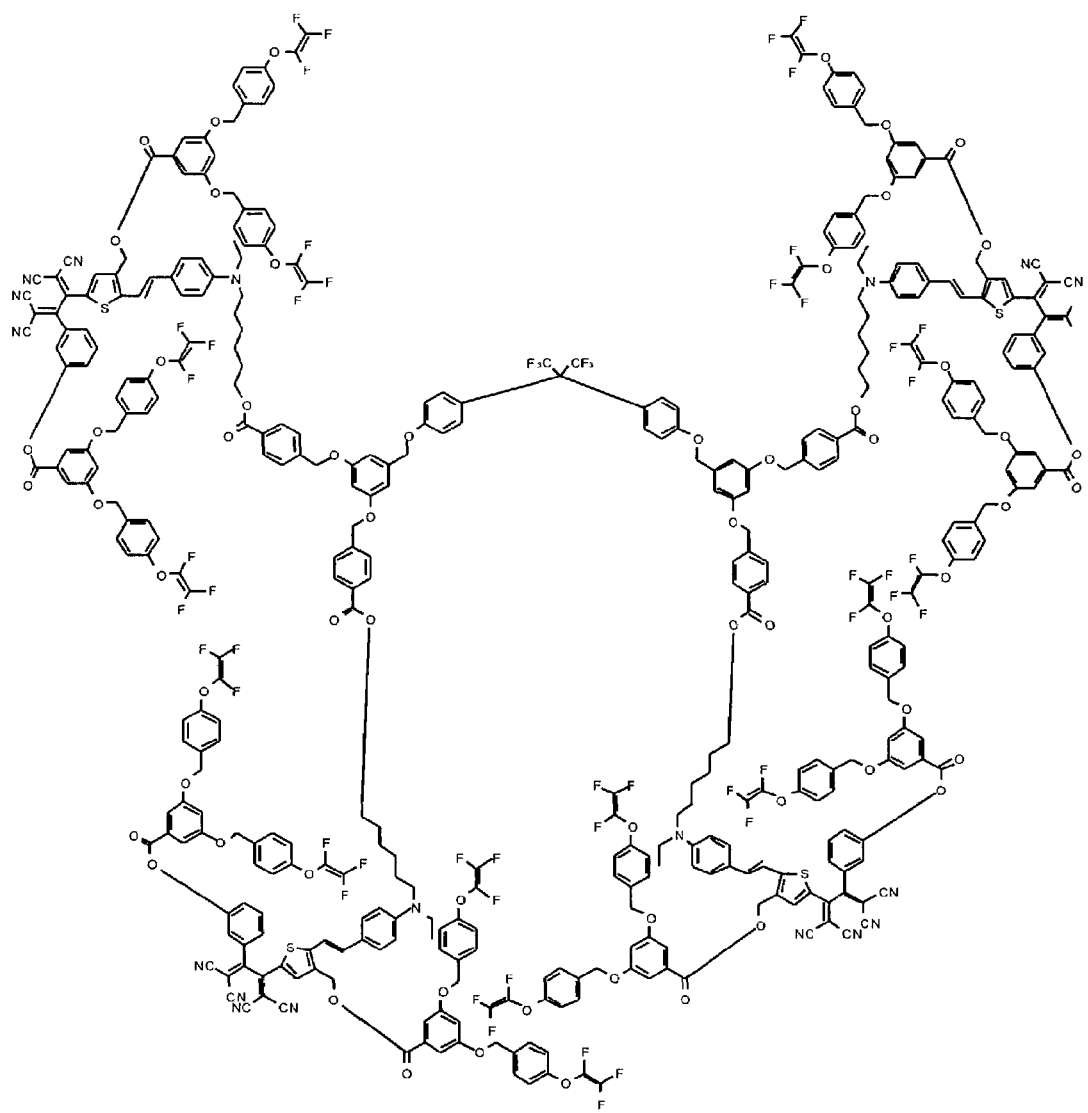
FIG. 9 is the chemical structure of a representative multi-chromophoric dendrimer of the invention.
Figure 10:
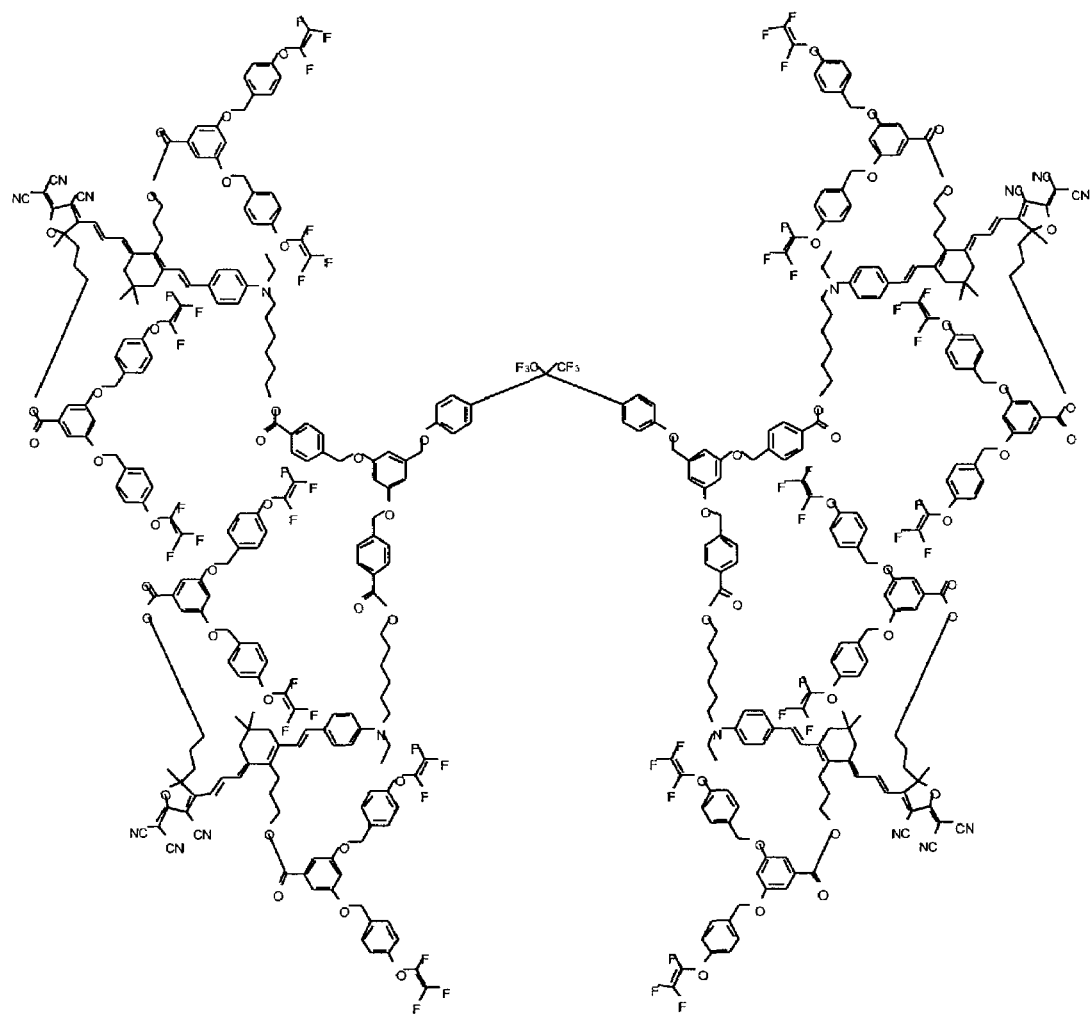
FIG. 10 is the chemical structure of a representative multi-chromophoric dendrimer of the invention.
Figure 11:
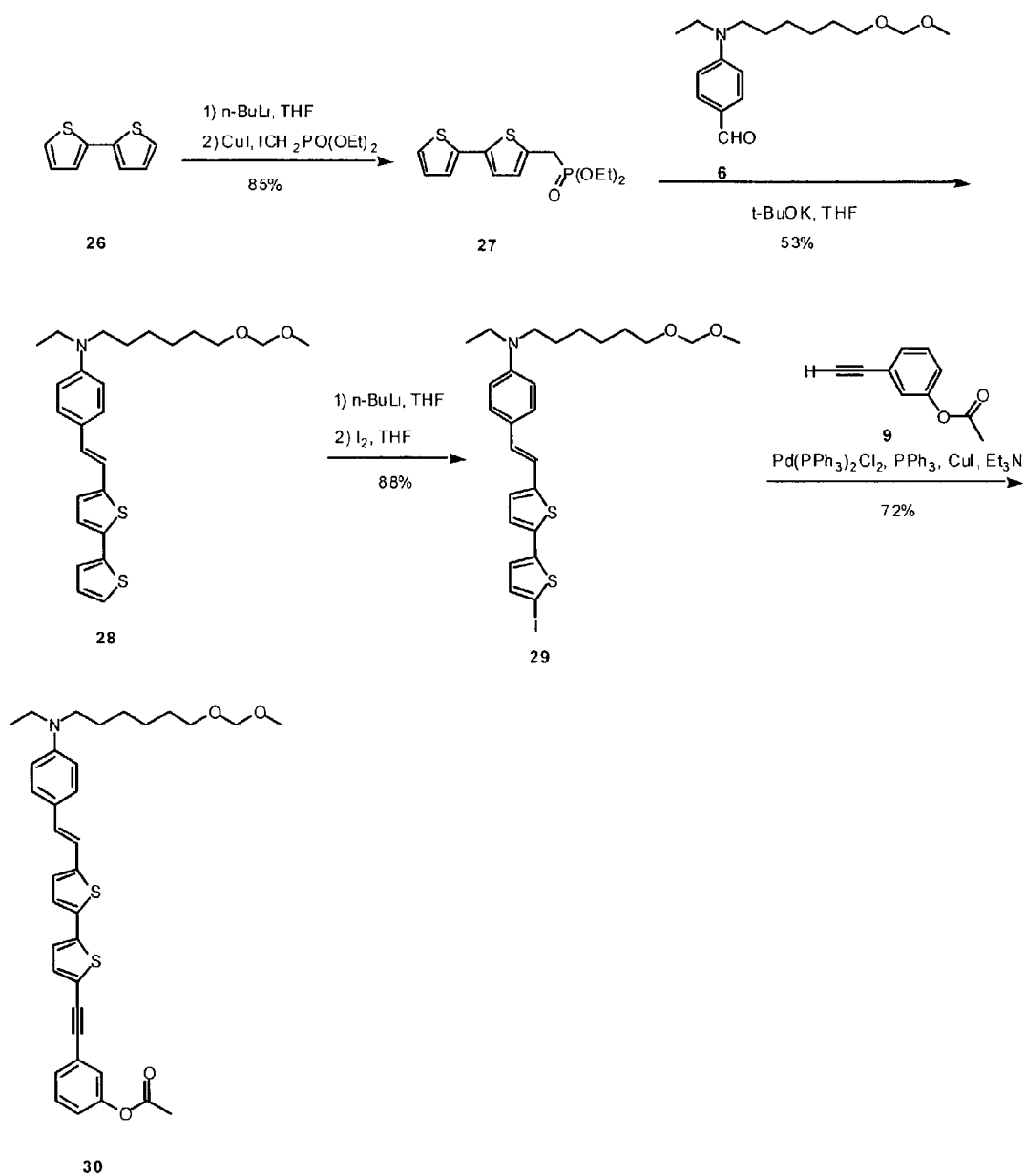
FIGS. 11-13 are a schematic illustration of the synthesis of a representative multi-chromophoric dendrimer of the invention.
Figure 12:
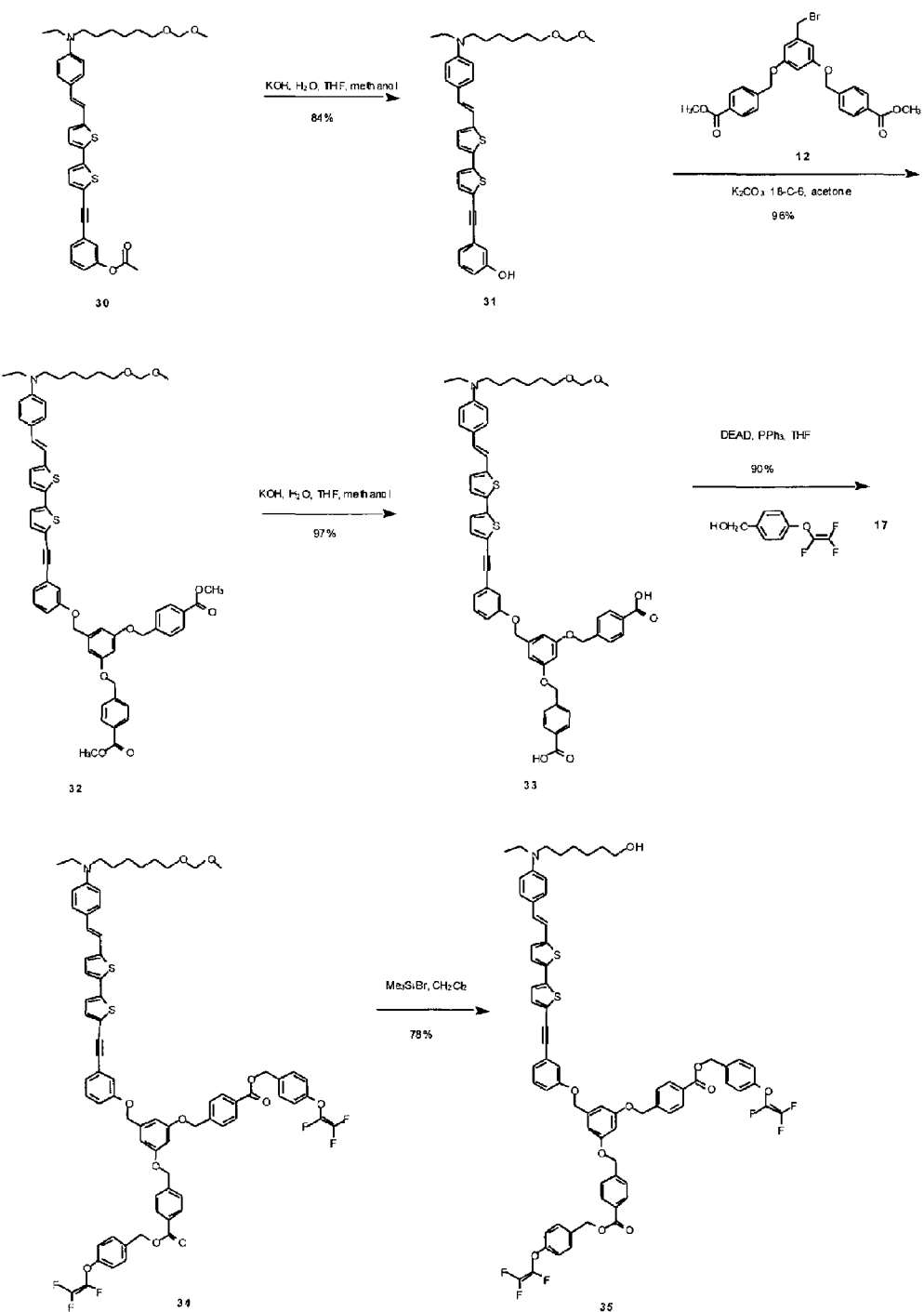
Figure 13:
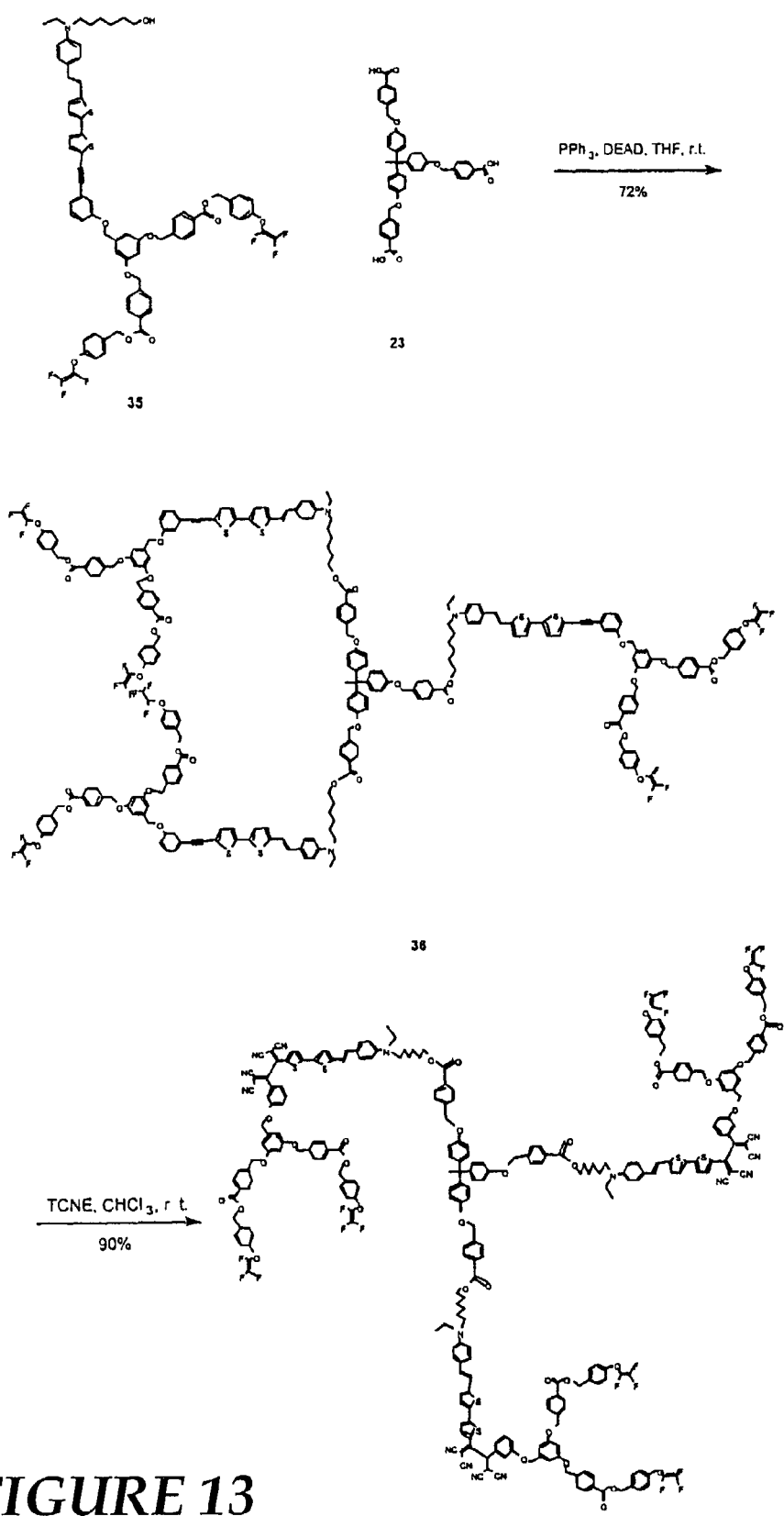

The synthesis of a representative crosslinkable dendrimer that includes a bithiophene bridge is described in Example 2 and illustrated schematically in FIGS. 11-13. Other representative multi-chromophoric dendrimers of the invention are illustrated in FIGS. 8-10. These dendrimers can be prepared by methods similar to those described in Examples 1 and 2. Another representative crosslinkable multi-chromophoric dendrimer is described in Example 4 and illustrated in FIG. 18.

Figure 16:
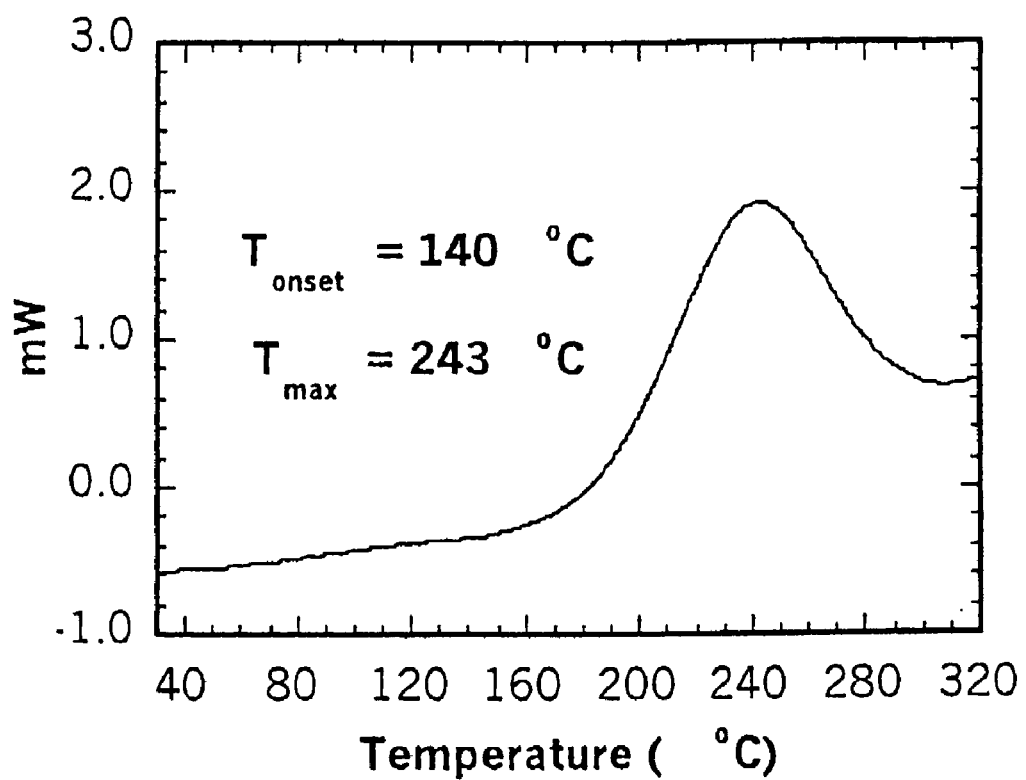
FIG. 16 is a schematic illustration of the synthesis of representative crosslinkable chromophores of the invention and their related polymers.

The syntheses of representative crosslinkable chromophores of the invention, their related macrostructures, and their E-O properties are described in Example 3 and illustrated in FIG. 16.

The materials and methods described herein can be useful in a variety of electro-optic applications. In addition, these materials and methods may be applied to polymer transistors or other active or passive electronic devices, as well as OLED (organic light emitting diode) or LCD (liquid crystal display) applications.

The use of organic polymers in integrated optics and optical communication systems containing optical fibers and routers has been previously described. The compounds, molecular components, polymers, and compositions (hereinafter, "materials") may be used in place of currently used materials, such as lithium niobate, in most type of integrated optics devices, optical computing applications, and optical communication systems. For instance, the materials may be fabricated into switches, modulators, waveguides, or other electro-optical devices.

For example, in optical communication systems devices fabricated from the multi-chromophoric dendrimers according to the present invention may be incorporated into routers for optical communication systems or waveguides for optical communication systems or for optical switching or computing applications. Because the materials are generally less demanding than currently used materials, devices made from such polymers may be more highly integrated, as described in U.S. Pat. No. 6,049,641, which is incorporated herein by reference. Additionally, such materials may be used in periodically poled applications as well as certain displays, as described in U.S. Pat. No. 5,911,018, which is incorporated herein by reference.

Techniques to prepare components of optical communication systems from optically transmissive materials have been previously described, and may be utilized to prepare such components from materials provided by the present invention. Many articles and patents describe suitable techniques, and reference other articles and patents that describe suitable techniques, where the following articles and patents are exemplary:

L. Eldada and L. Shacklette, "Advances in Polymer Integrated Optics," *IEEE Journal of Selected Topics in Quantum Electronics*, Vol. 6, No. 1, pp. 54-68 (January/February 2000); E. L. Wooten, et al. "A Review of Lithium Niobate Modulators for Fiber-Optic Communication Systems," *IEEE Journal of Selected Topics in Quantum Electronics*, Vol. 6, No. 1, pp. 69-82 (January/February 2000); F. Heismann, et al. "Lithium niobate integrated optics: Selected contemporary devices and system applications," *Optical Fiber Telecommunications III B*, Kaminow and Koch, eds. New York: Academic, pp. 377-462 (1997); E. Murphy, "Photonic switching," *Optical Fiber Telecommunications III B*, Kaminow and Koch, eds. New York: Academic, pp. 463-501 (1997); E. Murphy, *Integrated Optical Circuits and Components: Design and Applications*, New York: Marcel Dekker (August 1999); L. Dalton et al., "Polymeric Electro-optic Modulators: From Chromophore Design to Integration with Semiconductor Very Large Scale Integration Electronics and Silica Fiber Optics," *Ind. Eng. Chem. Res.*, Vol. 38, pp. 8-33 (1999); L. Dalton et al., "From molecules to opto-chips: organic electro-optic materials," *J. Mater. Chem.*, Vol. 9, pp. 1905-1920 (1999); I. Liakatas et al., "Importance of intermolecular interactions in the nonlinear optical properties of poled polymers," *Applied Physics Letters*, Vol. 76, No. 11, pp. 1368-1370 (13 Mar. 2000); C. Cai et al., "Donor-Acceptor-Substituted Phenylethenyl Bithiophenes: Highly Efficient and Stable Nonlinear Optical Chromophores," *Organic Letters*, Vol. 1, No. 11 pp. 1847-1849 (1999); J. Razna et al., "NLO properties of polymeric Langmuir-Blodgett films of sulfonamide-substituted azobenzenes," *J. of Materials Chemistry*, Vol. 9, pp. 1693-1698 (1999); K. Van den Broeck et al., "Synthesis and nonlinear optical properties of high glass transition polyimides," *Macromol. Chem. Phys.* Vol. 200, pp. 2629-2635 (1999); H. Jiang, and A. K. Kakkar, "Functionalized Siloxane-Linked Polymers for Second-Order Nonlinear Optics," *Macromolecules*, Vol. 31, pp. 2501-2508 (1998); A. K.-Y. Jen, "High-Performance Polyquinolines with Pendent High-Temperature Chromophores for Second-Order Nonlinear Optics," *Chem. Mater.*, Vol. 10, pp. 471-473 (1998); "Nonlinear Optics of Organic Molecules and Polymers," Hari Singh Nalwa and Seizo Miyata (eds.), CRC Press (1997); Cheng Zhang, Ph.D. Dissertation, University of Southern California (1999); Galina Todorova, Ph.D. Dissertation, University of Southern California (2000); U.S. Pat. Nos. 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,408,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514,799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091; 5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,966,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,322; and 6,091,879.

The foregoing references provide instruction and guidance to fabricate waveguides from materials generally of the types described herein using approaches such as direct photolithography, reactive ion etching, excimer laser ablation, molding, conventional mask photolithography, ablative laser writing, or embossing (e.g., soft embossing). The foregoing references also disclose electron acceptors, electron donors and electron bridges that may be incorporated into multi-chromophoric dendrimers according to the present invention or that may also incorporate an electron acceptor and/or electron donor and/or electron bridges described herein.

Components of optical communication systems that may be fabricated, in whole or part, with materials according to the present invention include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings. The materials described herein may be used with, for example, wafer-level processing, as applied in, for example, vertical cavity surface emitting laser (VCSEL) and CMOS technologies.

In many applications, the materials described herein may be used in lieu of lithium niobate, gallium arsenide, and other inorganic materials that currently find use as light-transmissive materials in optical communication systems.

The materials described herein may be used in telecommunication, data communication, signal processing, information processing, and radar system devices and thus may be used in communication methods relying, at least in part, on the optical transmission of information. Thus, a method according to the present invention may include communicating by transmitting information with light, where the light is transmitted at least in part through a material including a multi-chromophoric dendrimer or related macrostructure.

The materials of the present invention can be incorporated into various electro-optical devices. Accordingly, in another aspect, the invention provides electro-optic devices including the following.

An electro-optical device comprising a multi-chromophoric dendrimer or related macrostructure according to the present invention;

A waveguide comprising a multi-chromophoric dendrimer or related macrostructure according to the present invention;

An optical switch comprising a multi-chromophoric dendrimer or related macrostructure according to the present invention;

An optical modulator comprising a multi-chromophoric dendrimer or related macrostructure according to the present invention;

An optical coupler comprising a multi-chromophoric dendrimer or related macrostructure according to the present invention;

An optical router comprising a multi-chromophoric dendrimer or related macrostructure according to the present invention;

A communications system comprising a multi-chromophoric dendrimer or related macrostructure according to the present invention;

A method of data transmission comprising transmitting light through or via a multi-chromophoric dendrimer or related macrostructure according to the present invention;

A method of telecommunication comprising transmitting light through or via a multi-chromophoric dendrimer or related macrostructure according to the present invention;

A method of transmitting light comprising directing light through or via a multi-chromophoric dendrimer or related macrostructure according to the present invention;

A method of routing light through an optical system comprising transmitting light through or via a multi-chromophoric dendrimer or related macrostructure according to the present invention;

An interferometric optical modulator or switch, comprising: (1) an input waveguide; (2) an output waveguide; (3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end, wherein at least one of the first and second legs includes a multi-chromophoric dendrimer or related macrostructure according to the present invention;

An optical modulator or switch, comprising: (1) an input; (2) an output; (3) a first waveguide extending between the input and output; and (4) a second waveguide aligned to the first waveguide and positioned for evanescent coupling to the first waveguide; wherein at least one of the first and second legs includes a multi-chromophoric dendrimer or related macrostructure according to the present invention. The modulator or switch may further including an electrode positioned to produce an electric field across the first or second waveguide;

An optical router comprising a plurality of switches, wherein each switch includes: (1) an input; (2) an output; (3) a first waveguide extending between the input and output; and (4) a second waveguide aligned to the first waveguide and positioned for evanescent coupling to the first waveguide; wherein at least one of the first and second legs includes a multi-chromophoric dendrimer or related macrostructure according to the present invention. The plurality of switches may optionally be arranged in an array of rows and columns.

The following examples are provided for the purpose of illustrating, not limiting, the invention.

EXAMPLES

Example 1

Representative Multi-Chromophoric Dendrimer

Phenyl Tetracyanobutadiene Acceptor with Thiophene Bridge

In this example, the preparation and electro-optic properties of a representative multi-chromophoric dendrimer of the invention is described. The dendrimer includes three chromophores, each having an amino benzene donor, phenyl tetracyanobutadine acceptor, and thiophene bridge. The dendrimer also includes crosslinkable trifluorovinyl ether groups at the dendrimer's periphery. The synthetic procedures are illustrated in FIGS. 3-6.

To a well stirred solution of N-ethylaniline 1 (38.0 g, 0.31 mol) in n-butanol (200 mL) at room temperature, 6-chlorohexanol 2 (44.56 g, 0.33 mol) was added dropwise followed by the addition of potassium carbonate (45.00 g) and potassium iodide (cat. 1.40 g) with portions. After addition, the mixture was stirred at room temperature for 1 h and later refluxed for 96 h. At this time, the reaction mixture was cooled and filtered. The resulting solid was washed with ethanol. The filtrates were combined and concentrated. The oil was purified through a packed chromatographic column and eluted with hexane/ethyl acetate (5:1) with a gradient to (2:1) to afford the desired hydroxyaniline 3 as a viscous oil (63.8 g, 92%).

To a well stirred solution of 3 (50.0 g, 0.226 mol) in diisopropylethylamine (150 mL) at 0° C., chloromethylmethyl ether (18.7 mL, 20.0 g, 0.248 mol) was added dropwise. After the addition was complete the mixture was brought to room temperature and stirred overnight. At this time, water (3.0 mL) was added and stirred for 20 min. Then the solvent was removed under reduced pressure. Then hexane (150 mL) was added, the insoluble white solid was filtered, and washed with additional hexane. The hexane filtrates were combined and washed with water, dried over anhydrous sodium sulfate. Evaporation of solvents gave a viscous oil, which was dried under vacuum to give pure 4 (54.97 g, 92%).

Compound 4 (54.97 g, 0.207 mol) was dissolved in DMF (150 mL) and was stirred at r.t. for 20 min. A solution of N-bromosuccinimide (36.87 g, 0.207 mol) in DMF (100 mL) was added dropwise. After the addition was completed, the reaction mixture was stirred overnight under an inert atmosphere. At this time, the reaction mixture was poured into 300 mL of ice cold water and the resulting mixture was extracted with hexane (2*300 mL). The organic layers were combined, dried over sodium sulfate. Evaporation of solvent gave a brown oil which is dried under vacuum overnight to the desired compound 5 (66.25 g, 96%).

To a cooled solution at −78° C. of 5 (22.5 g, 65.4 mmol) in dry THF (100 mL) under nitrogen atmosphere was dropwise added t-BuLi (86 mL, 146.2 mmol, 1.7 M in pentane). The solution was stirred at −78° C. for 30 min and then dry DMF (7.3 g, 100 mmol) was added slowly. The resulting solution was allowed to warm up to room temperature. The reaction was quenched with water. The mixture was concentrated and was dissolved by water (250 mL). It was extracted with $CH_2Cl_2$ (2*300 mL) and the combined organic layers were dried over $Na_2SO_4$ and evaporated. The residue was purified by flash column chromatography eluting with hexane/ethyl acetate (7:1 to 2:1) to give 6 (15.11 g, 79%).

To the mixture of 6 (8.79 g, 30.0 mmol) and diethyl thiophenylmethylphosphate (7.49 g, 32.0 mmol) in dry THF (40 mL) at 0° C. under nitrogen atmosphere was added t-BuOK (3.70 g, 33.0 mmol) in dry THF (40 mL). The reaction mixture was stirred at room temperature for 3 h. The reaction was quenched with water. The mixture was concentrated and was dissolved by water (150 mL). It was extracted with $CH_2Cl_2$ (2*200 mL) and the combined organic layers were dried over $Na_2SO_4$ and evaporated. The crude product was purified by flash column chromatography eluting with hexane/ethyl acetate (10:1) to give a yellow solid 7 (11.03 g, 98%).

To a cooled solution at −78° C. of 7 (3.75 g, 10.0 mmol) in dry THF (20 mL) was dropwise added n-BuLi (4.4 mL, 11.0 mmol, 2.5 M) under nitrogen atmosphere. After the completion of this addition, the cooling bath was removed and the reaction mixture was warmed up to room temperature. Then the reaction flask was cooled back to −78° C. and the solution was transferred via cannula to another reaction flask containing 12 (2.54 g, 10.0 mmol) in THF (5 mL) at ca. −20° C. The reaction mixture was allowed to stir at room temperature for 30 min before quenching by 5% $NaHSO_3$ aqueous solution. The crude product was extracted with hexane and then $CH_2Cl_2$. The combined organic layers were dried over $Na_2SO_4$ and evaporated. The residue was separated by flash column chromatography eluting with hexane/ethyl acetate (7:1) to give a brownish solid 8 (3.95 g, 79%).

The mixture of 8 (3.95 g, 7.9 mmol), 3-acetoxylphenyl acetylene (1.28 g, 8.0 mmol), $Pd(PPh_3)_4$ (80 mg), $PPh_3$ (40 mg) and CuI (40 mg) in diethylamine (20 mL) was stirred overnight under nitrogen at 30° C. The diethylamine was evaporated and the residue was separated by column chromatography eluting with hexane/ethyl acetate (7:1 to 4:1) to afford a red solid 9 (3.57 g, 85%).

To a solution of 9 (4.35 g, 8.2 mmol) in tetrahydrofuran (103 mL) was added potassium hydroxide (8.72 g, 155.4 mmol) dissolved in water (12.5 mL). Methanol (41 mL) was then added to this two-phase system to give a homogenous solution. The solution was then heated at reflux for 3 h. The reaction mixture was cooled to room temperature and acidified with glacial acetic acid (20 mL). The solution was concentrated by rotary evaporation and partitioned between water and ether, and the aqueous layer was extracted with ether for three times. The combined extracts were dried over sodium sulfate and evaporated. The crude product was purified by flash column chromatography eluting with methylene chloride/ethyl acetate (10:1) to give a yellow solid 10 (3.64 g, 91%).

A mixture of methyl 4-(bromomethyl)benzoate (18.78 g, 82.0 mmol), 3,5-dihydroxybenzyl alcohol (5.61 g, 40.0 mmol), dried potassium carbonate (13.82 g, 100.0 mmol), and 18-crown-6 (2.11 g, 8.0 mmol) in dry acetone was heated at reflux and stirred vigorously under nitrogen for 48 h. The mixture was allowed to cool and evaporated to dryness under reduced pressure. The residue was partitioned between water and $CH_2Cl_2$ and the aqueous layer extracted with $CH_2Cl_2$ for three times. The combined organic layers were then dried and evaporated to dryness. The crude product was purified by column chromatography eluting with $CH_2Cl_2$ to $CH_2Cl_2$/ethyl acetate (9:1) to afford a white solid 11 (16.10 g, 92%).

To a mixture of the 11 (11.23 g, 25.7 mmol) and carbon tetrabromide (10.65 g, 32.1 mmol) in the minimum amount of dry tetrahydrofuran required to dissolve the above reagents was added triphenylphosphine (8.42 g, 32.1 mmol), and the reaction mixture was stirred under nitrogen for 20 min. The reaction mixture was then poured into water and extracted with $CH_2Cl_2$ for three times; the combined extracts were dried and evaporated to dryness. The crude product was purified by column chromatography eluting with hexane/$CH_2Cl_2$ (1:1) to $CH_2Cl_2$ to afford a white solid 12 (8.09 g, 63%).

A mixture of 10 (3.06 g, 6.2 mmol), 12 (3.27 g, 6.6 mmol), potassium carbonate (1.08 g, 7.8 mmol) and 18-crown-6 (0.33 g, 1.3 mmol) in acetone (50 mL) was heated at reflux and stirred vigorously under nitrogen for 24 h. The mixture was allowed to cool and rotary evaporated to dryness under reduced pressure. The residue was partitioned between water and methylene chloride, and the aqueous layer was extracted with methylene chloride for three times. The combined extracts were dried over sodium sulfate and evaporated. The crude product was purified by flash column chromatography eluting with methylene chloride/ethyl acetate (50:1) to give a viscous yellow liquid 13 (4.63 g, 82%).

To a solution of 13 (4.62 g, 5.1 mmol) in tetrahydrofuran (128 mL) was added potassium hydroxide (10.85 g, 193.4 mmol) dissolved in water (15.7 mL). Methanol (51 mL) was then added to this two-phase system to give a homogenous solution. The solution was then heated at reflux for 3.5 h. The reaction mixture was cooled to room temperature and acidified with glacial acetic acid (51 mL). The solution was concentrated by rotary evaporation and partitioned between water and ethyl acetate, and the aqueous layer was extracted with ethyl acetate for three times. The combined extracts were dried over sodium sulfate, evaporated and dried to give a yellow solid 14 (4.10 g, 92%).

A 250-mL, three-neck, round-bottom flask, equipped with a magnetic stirring bar, a $N_2$ inlet, a rubber septum, was purged with $N_2$ and charged with aryl bromide 15 (12.95 g, 51.2 mmol) and dry ether (77 mL). The mixture was cooled to −78° C., and t-Bu—Li (31.0 mL, 52.7 mmol, 1.7 M in pentane) was added dropwise from the syringe. The mixture was then stirred for ca. 1 h at −78° C. and dimethylformamide (DMF) (6.0 mL, 5.64 g, 76.8 mmol) was added dropwise to the above solution. The resulting mixture was stirred at the same temperature for 2 h and the mixture was allowed to warm up to room temperature during the next 1 h. At this time, water (2.3 mL) was added and the resulting mixture was stirred overnight. The mixture was concentrated under vacuum, then dissolved in water (195 mL) and extracted with methylene chloride for three times. The combined organic layer was dried over sodium sulfate, concentrated and purified by neutral alumina oxide column chromatography eluting with hexane/methylene chloride (5:1) and then with gradual increasing proportions of methylene chloride (to pure methylene chloride) to give a liquid 16 (5.20 g, 50%).

To a 500-mL two-neck flask equipped with a nitrogen inlet and a magnetic stirrer were added 16 (4.90 g, 24.2 mmol) and the mixture of benzene and ethanol (1:1, 300 mL) under nitrogen atmosphere. Sodium borohydride (1.19 g, 31.5 mmol) was added to the above solution. After stirring for t h at ambient temperature, the solvent was removed by rotary evaporation and the residual liquid was extracted with methylene chloride for three times. The combined organic layer was dried over sodium sulfate, concentrated and purified by neutral alumina oxide column chromatography eluting with methylene chloride and then with gradual increasing proportions of ethyl acetate (to pure ethyl acetate) to give a colorless liquid 17 (3.96 g, 80%).

Diacid 14 (4.02 g, 4.6 mmol), $PPh_3$ (2.88 g, 11.0 mmol) and 17 (2.05 g, 10.1 mmol) were dissolved in dry THF (60 mL) successively. The flask was flushed with dry nitrogen. Diethyl azodicarboxylate (DEAD) (1.73 mL, 1.91 g, 11.0 mmol) was added dropwise to the solution. The reaction mixture was further stirred at room temperature for 18 h. The solvent was removed by rotary evaporation and the residue was extracted with methylene chloride for three times. The combined organic layer was dried over sodium sulfate, concentrated and purified by neutral alumina oxide column chromatography eluting with hexane/methylene chloride (1:1) and then with gradual increasing proportions of methylene chloride (to pure methylene chloride) to give a yellow liquid 18 (4.10 g, 72%).

To a cooled solution at −30° C. of 18 (1.77 g, 1.4 mmol) in dry methylene chloride (15 mL) was added trimethylsilyl bromide (2.25 mL, 2.61 g, 17.0 mmol). The solution was stirred for 2 h at −30° C. The reaction mixture was poured into a solution of saturated sodium bicarbonate, then extracted with methylene chloride for three times. The combined organic layer was dried over sodium sulfate, concentrated and purified by neutral alumina oxide column chromatography eluting with hexane/methylene chloride (1:3) and then with gradual increasing proportions of methylene chloride (to pure methylene chloride) to give a yellow liquid 19 (1.43 g, 84%).

A mixture of 1,1,1-tris(4-hydroxyphenyl)ethane (4.60 g, 15.0 mmol), methyl 4-(bromomethyl)benzoate (10.65 g, 46.5 mmol, 3.1 equiv.), potassium carbonate (7.77 g, 56.3 mmol, 3.75 equiv.) and 18-crown-6. (1.19 g, 4.5 mmol, 0.3 equiv.) in acetone (120 mL) was heated at reflux and stirred vigorously under nitrogen for 48 h. The mixture was allowed to cool and rotary evaporated to dryness under reduced pressure. The residue was partitioned between water and methylene chloride, and the aqueous layer was extracted with methylene chloride for three times. The combined extracts were dried over sodium sulfate and evaporated. The crude product was purified by flash column chromatography eluting with methylene chloride and then with gradual increasing proportions of ethyl acetate (to 1:50 ethyl acetate/methylene chloride) to give a white solid 20 (11.22 g, 99%).

To a solution of 20 (5.26 g, 7.0 mmol) in tetrahydrofuran (280 mL) was added potassium hydroxide (22.39 g, 399.0 mmol) dissolved in water (34 mL). Methanol (110 mL) was then added to this two-phase system to give a homogenous solution. The solution was then heated at reflux for 6 h during which time a precipitate formed; the reaction mixture was then evaporated to dryness and the residue redissolved in a mixture of dimethyl sulfoxide (120 mL) and methanol (30 mL). Hydrochloric acid (6 N, 25 mL) was added dropwise to the above solution and the resulting mixture was poured into water (1500 mL). The precipitate which formed was collected by vacuum filtration and dried to give acid as a white solid 21 (4.60 g, 93%).

Triacid 21 (0.23 g, 0.33 mmol), PPh$_3$ (0.38 g, 1.43 mmol) and 19 (1.43 g, 1.19 mmol) were dissolved in dry THF (40 mL) successively. The flask was flushed with dry nitrogen. Diethyl azodicarboxylate (DEAD) (0.23 mL, 0.25 g, 1.43 mmol) was added dropwise to the solution. The reaction mixture was further stirred at room temperature for 18 h. The solvent was removed by rotary evaporation and the residue was extracted with methylene chloride for three times. The combined organic layer was dried over sodium sulfate, concentrated and purified by neutral alumina oxide column chromatography eluting with hexane/methylene chloride (1:1) and then with gradual increasing proportions of methylene chloride (to pure methylene chloride) to give a yellow solid 22 (0.97 g, 69%).

A mixture of 22 (0.94 g, 0.22 mmol) and tetracyanoethylene (TCNE) (84.5 mg, 0.66 mmol) in chloroform (20 mL) was stirred at room temperature for 24 h. The solution was rotary evaporated to dryness, and the resulting solid was extracted with hexane for 12 h and with methanol for 12 h to give a blue powder 23 (0.89 g, 86%).

Figure 14:
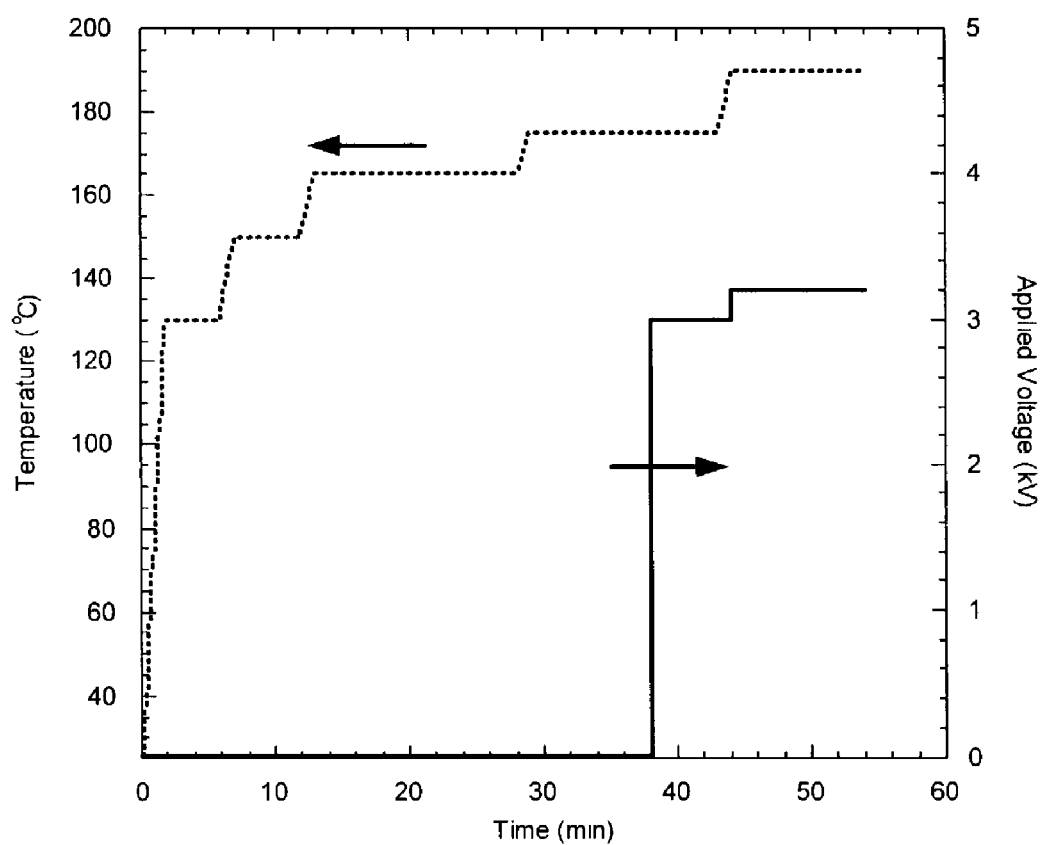
FIG. 14 is a graph illustrating a curing/poling profile for a representative crosslinkable multi-chromophoric dendrimer of the invention.
Figure 15:
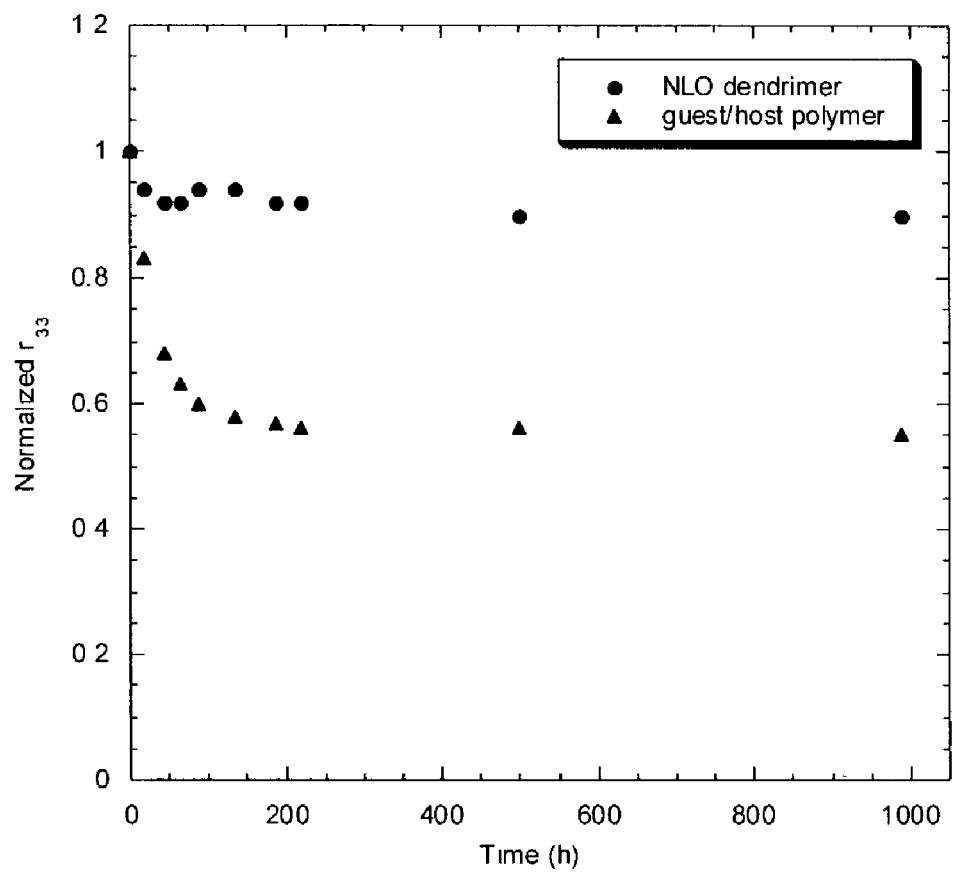
FIG. 15 is a graph comparing the temporal stability of a representative poled and crosslinked multi-chromophoric dendrimer of the invention and a noncrosslinkable multi-chromophoric dendrimer in a guest/host polymer system.

For E-O measurements, the solution of 23 in mesitylene/cyclopentanone (22 w/w % solution, filtered through a 0.2 μm syringe filter) was spin-coated onto an indium tin oxide (ITO) glass substrate. The film was heated under vacuum at 120° C. overnight to remove residual solvent. The dipole alignment was achieved by corona poling and the $r_{33}$ value was measured using a simple reflection technique at 1.55 μm. After sequential heating (at 130° C. for 4 min, 150° C. for 5 min, 165° C. for 15 min and 175° C. for 8 min) and poling (with 3.0 kV at 175° C. for 6 min and 3.2 kV at 190° C. for 10 min) (FIG. 14), a very large E-O coefficient ($r_{33}$=60 pm/V) at 1.55 μm was achieved. The resulting poled dendrimer also possessed excellent temporal stability that retained >90% of its original $r_{33}$ value at 85° C. for more than 1000 h (FIG. 15).

Example 2

Representative Multi-Chromophoric Dendrimer

Phenyl Tetracyanobutadiene Acceptor with Bithiophene Bridge

In this example, the preparation and electro-optic properties of a representative multi-chromophoric dendrimer of the invention is described. The dendrimer includes three chromophores, each having an amino benzene donor, phenyl tetracyanobutadine acceptor, and bithiophene bridge. The dendrimer also includes crosslinkable trifluorovinyl ether groups at the dendrimer's periphery. The synthetic procedures are illustrated in FIGS. 11-13.

To a stirred solution of bithiophene (1.66 g, 10 mmol) in dry THF (32 mL) was added n-BuLi (4.2 mL, 10.5 mmol, 2.5 M) at −78° C. under nitrogen atmosphere. The solution was stirred at −78° C. for 1 h, and then transferred via cannula into a flask containing CuI (1.90 g, 10.0 mmol) cooled in dry ice bath. After the stirring at room temperature for 2 h, diethyl iodomethylphosphate (2.78 g, 10 mmol) was added. The reaction mixture was stirred at r.t. overnight. The reaction was worked up by pouring the reaction solution onto ice with some Na$_2$S crystal. The mixture was extracted with ethyl ether (2*100 mL). The combined organic layers was dried over Na$_2$SO$_4$ and evaporated. The crude product was purified by flash column chromatography eluting with CH$_2$Cl$_2$ and then ethyl acetate to give a clear yellow oil 27 (2.69 g, 85%).

To the mixture of 6 (1.82 g, 6.2 mmol) and 27 (1.96 g, 6.2 mmol) in dry THF (30 mL) at 0° C. under nitrogen atmosphere was added t-BuOK (6.2 mL, 6.2 mmol, 1.0 M in THF). The reaction mixture was stirred at room temperature for 3 h. The reaction was quenched with water. The mixture was concentrated and was dissolved by water (100 mL). It was extracted with CH$_2$Cl$_2$ (2*150 mL) and the combined organic layers were dried over Na$_2$SO$_4$ and evaporated. The crude product was purified by flash column chromatography eluting with hexane/ethyl acetate (10:1) to 28 (1.50 g, 53%).

To a cooled solution at −78° C. of 28 (4.79 g, 10.5 mmol) in dry THF (60 mL) was dropwise added n-BuLi (4.4 mL, 11.0 mmol, 2.5 M) under nitrogen atmosphere. After the stirring at −78° C. for 10 min, the cooling bath was removed and the reaction mixture was warmed up to room temperature, and stirred at room temperature for 10 min. Then the reaction flask was cooled back to −78° C. and the solution was transferred to another reaction flask containing I$_2$ (2.79 g, 11.0 mmol) in THF (10 mL) at ca. −20° C. The reaction mixture was allowed to stir at room temperature for 45 min before quenching by 5% NaHSO$_3$ aqueous solution. The crude product was extracted with CH$_2$Cl$_2$. The combined organic layers were dried over Na$_2$SO$_4$ and evaporated. The residue was separated by flash column chromatography eluting with hexane/ethyl acetate (7:1) to give a yellow solid 29 (5.42 g, 88%).

The mixture of 29 (3.58 g, 6.2 mmol), 3-acetoxylphenyl acetylene 9 (1.08 g, 6.7 mmol), Pd(PPh$_3$)$_2$Cl$_2$ (261 mg), PPh$_3$ (355 mg) and CuI (129 mg) in triethylamine (40 mL) was refluxed under nitrogen for 2.5 h. The triethylamine was evaporated and the crude product was extracted with CH$_2$Cl$_2$, dried over Na$_2$SO$_4$ and concentrated. The residue was separated by column chromatography eluting with hexane/ethyl acetate (7:1 to 4:1) to afford a brown solid 30 (2.73 g, 72%).

To a solution of 30 (2.67 g, 4.35 mmol) in tetrahydrofuran (55 mL) was added potassium hydroxide (4.64 g, 82.65 mmol) dissolved in water (6.6 mL). Methanol (22 mL) was then added to this two-phase system to give a homogenous solution. The solution was then heated at reflux for 3 h. The reaction mixture was cooled to room temperature and acidified with glacial acetic acid (15 mL). The solution was concentrated by rotary evaporation and partitioned between water and ether, and the aqueous layer was extracted with ether for three times. The combined extracts were dried over sodium sulfate and evaporated. The crude product was purified by flash column chromatography eluting with methylene chloride/ethyl acetate (10:1) to give a solid 31 (2.10 g, 84%).

A mixture of 31 (2.08 g, 3.64 mmol), 12 (1.91 g, 3.82 mmol), potassium carbonate (0.63 g, 4.55 mmol) and 18-crown-6 (0.19 g, 0.73 mmol) in acetone (50 mL) was heated at reflux and stirred vigorously under nitrogen for 24 h. The mixture was allowed to cool and rotary evaporated to dryness under reduced pressure. The residue was partitioned between water and methylene chloride, and the aqueous layer was extracted with methylene chloride for three times. The combined extracts were dried over sodium sulfate and evaporated. The crude product was purified by flash column chromatography eluting with methylene chloride/ethyl acetate (50:1) to give a red solid 32 (3.44 g, 96%).

To a solution of 32 (3.44 g, 3.47 mmol) in tetrahydrofuran (87 mL) was added potassium hydroxide (7.40 g, 131.9 mmol) dissolved in water (10.7 mL). Methanol (35 mL) was then added to this two-phase system to give a homogenous solution. The solution was then heated at reflux for 3.5 h. The reaction mixture was cooled to room temperature and acidified with glacial acetic acid (35 mL). The solution was concentrated by rotary evaporation and partitioned between water and ethyl acetate, and the aqueous layer was extracted with ethyl acetate for three times. The combined extracts were dried over sodium sulfate, evaporated and dried to give a orange solid 33 (3.25 g, 97%).

A mixture of 33 (3.22 g, 3.34 mmol), PPh$_3$ (2.10 g, 8.04 mmol) and 17 (1.50 g, 7.35 mmol) were dissolved in dry THF (50 mL) successively. The flask was flushed with dry nitrogen. Diethyl azodicarboxylate (DEAD) (1.26 mL, 1.40 g, 8.02 mmol) was added dropwise to the solution. The reaction mixture was further stirred at room temperature for 24 h. The solvent was removed by rotary evaporation and the residue was extracted with methylene chloride for three times. The combined organic layer was dried over sodium sulfate, concentrated and purified by neutral alumina oxide column chromatography eluting with hexane/methylene chloride (1:1) and then with gradual increasing proportions of methylene chloride (to pure methylene chloride) to give a red solid 34 (4.02 g, 90%).

To a cooled solution at −30° C. of 34 (2.67 g, 2.00 mmol) in dry methylene chloride (15 mL) was added trimethylsilyl bromide (2.11 mL, 2.45 g, 16.0 mmol). The solution was stirred for 2 h at −30° C. The reaction mixture was poured into a solution of saturated sodium bicarbonate, then extracted with methylene chloride for three times. The combined organic layer was dried over sodium sulfate, concentrated and purified by neutral alumina oxide column chromatography eluting with hexane/methylene chloride (1:3) and then with gradual increasing proportions of methylene chloride (to pure methylene chloride) to give a red viscous liquid 35 (1.40 g, 78%).

A mixture of 23 (0.215 g, 0.303 mmol), PPh$_3$ (0.344 g, 1.31 mmol) and 35 (1.40 g, 1.09 mmol) were dissolved in dry THF (40 mL) successively. The flask was flushed with dry nitrogen. Diethyl azodicarboxylate (DEAD) (0.21 mL, 0.23 g, 1.31 mmol) was added dropwise to the solution. The reaction mixture was further stirred at room temperature for 22 h. The solvent was removed by rotary evaporation and the residue was extracted with methylene chloride for three times. The combined organic layer was dried over sodium sulfate, concentrated and purified by neutral alumina oxide column chromatography eluting with hexane/methylene chloride (1:1) and then with gradual increasing proportions of methylene chloride (to pure methylene chloride) to give a red solid 36 (0.98 g, 72%).

A mixture of 24 (0.96 g, 0.21 mmol) and tetracyanoethylene (TCNE) (81.8 mg, 0.64 mmol) in chloroform (20 mL) was stirred at room temperature for 24 h. The solution was rotary evaporated to dryness, and the resulting solid was extracted with hexane for 12 h and with methanol for 12 h to give a blue powder 37 (0.89 g, 90%).

Example 3

Representative Crosslinkable Chromophores and Related Macrostructures

Perfluorocyclobutyl Thermoset Polymers

In this example, the preparation and properties of a representative crosslinkable chromophores and their related macrostructures are described. The chromophores include crosslinkable trifluorovinyl ether groups and the macrostructure is a perfluorocyclobutane-containing thermoset polymer.

Figure 17:
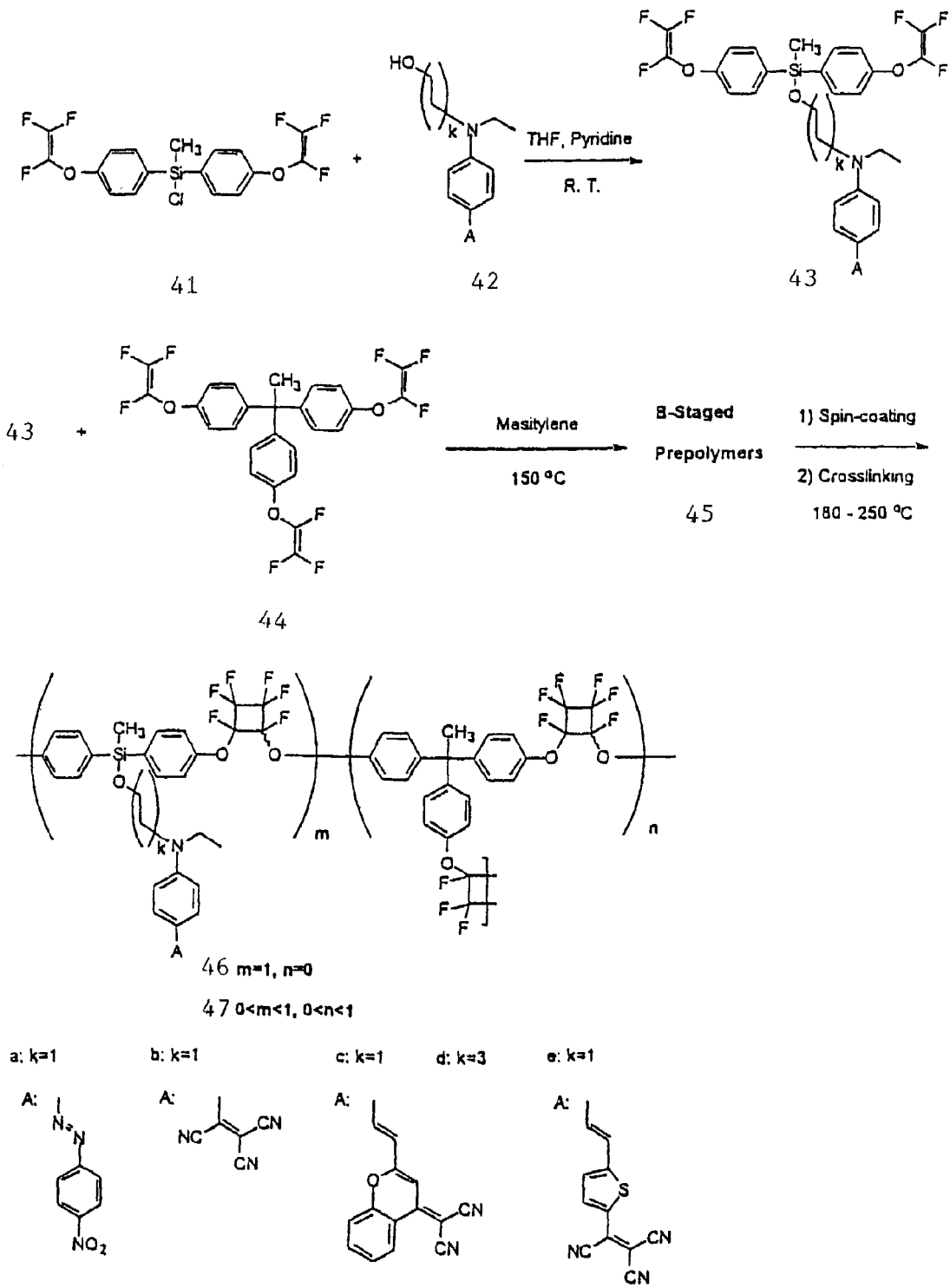
FIG. 17 is a differential scanning calorimetry graph illustrating the homopolymerization of representative crosslinkable chromophores of the invention.

NLO chromophore-containing monomers were prepared in high yield by condensation reaction between di(trifluorovinylether)mesityl chloride and hydroxy-containing chromophores as illustrated in FIG. 16. Exothermic cyclodimerization of trifluorovinylether groups in these chromophores was typically detected at about 140° C. by differential scanning calorimeter (DSC) (10° C./min) with reaction profiles similar to that of general di(trifluorovinylether) compounds. For example, the reaction of 43c showed a peak polymerization temperature at 243° C. and gave an enthalpy of −16 kcal/mol per perfluorolinkage. The homopolymerization by DSC is illustrated in FIG. 17.

As a result, polymerization was accomplished by simply heating the monomers or the solution of monomers under an inert atmosphere at about 150° C. The chromophore remains intact because the polymerization process is a radical-mediated stepwise addition process that is followed by a rapid ring cyclization, which is quite different from conventional radical and condensation polymerization.

The polymers obtained by bulk polymerization of the monomers at 180° to 250° C. possessed relatively low Tg in the range of 90° to 140° C. due to high chromophore concentrations (38-51 weight percent). In order to adjust the chromophore density to a suitable level for poling, the monomers 43 and 44 (see FIG. 16) were copolymerized at 150° C. in mesitylene at a solution concentration of about 35-45 weight percent to yield reactive oligomer/monomer mixtures with controlled molecular weights. The B-staged prepolymers 45 possessed good solubility in the mixture of mesitylene and cyclopentanone (30-40% w/w). Optical quality films can be prepared from these solutions. The prepolymers have low Tg or melting points that allow them to be melted, reflowed, and efficiently crosslinked in thin films at 180° to 250° C. All of the perfluorocyclobutyl (PFCB) thermoset polymers have high Tg (>180° C.) and excellent thermal stability. Weight losses of less than 3 percent up to 350° C. were observed by thermogravimetric analysis (TGA) for the polymers. The PFCB thermoset polymers possessed excellent solvent resistance, which is highly desirable for multilayer process in the fabrication of E-O devices.

TABLE 2

Properties of Thermoset PFCB Polymers.

| Polymers | Chromophore density (w/w %) | T (° C.) | λ (cm) | n TE | n TM | Loss (dB/cm) |
|---|---|---|---|---|---|---|
| 47b | 30 | 185 | 506 | 1.5855 | 1.5840 | 6.0 |
| 47c | 25 | 230 | 502 | 1.5670 | 1.5634 | 2.8 |
| 47d | 2.0 | 195 | 511 | 1.5454 | 1.5413 | 2.4 |
| 47e | 25 | 192 | 636 | 1.5752 | 1.5711 | 2.9 |

The polymers have refractive indices ranging from 1.541 to 1.586 with low birefringence (0.002-0.004) and optical loss (2-3 dB/m) for polymers 47c-d at 0.83 um polymer 47e at 1.3 um. For E-O measurements, the B-staged prepolymer solutions in mesitylene/cyclopentanone (30-40% w/w solution filtered through a 0.2 um syringe filter) were spin-coated onto an indium tin oxide (ITO) glass substrate. The films were heated in a vacuum oven at 180° C. for 0.5 hour to ensure removal of the residual solvent. The reactive prepolymers were advanced by heating at 190° to 250° C. under nitrogen.

The dipole alignments in the polymers were achieved by contact poling. Poling results indicated that the thermoset PFCB polymers possessed large $r_{33}$ and good temporal stability. Polymer 47c exhibited an $r_{33}$ value of 21 pm/V at 1.3 um under a poling field of 1.0 MV/cm. The $r_{33}$ value of polymer 47e retained approximately 80 percent of its original value at 85° C. for more than 1000 hours.

Example 4

Representative Multi-Chromophoric Dendrimer and Related Macrostructure

Perfluorocyclobutyl Dendrimer Macrostructure

Figure 18:
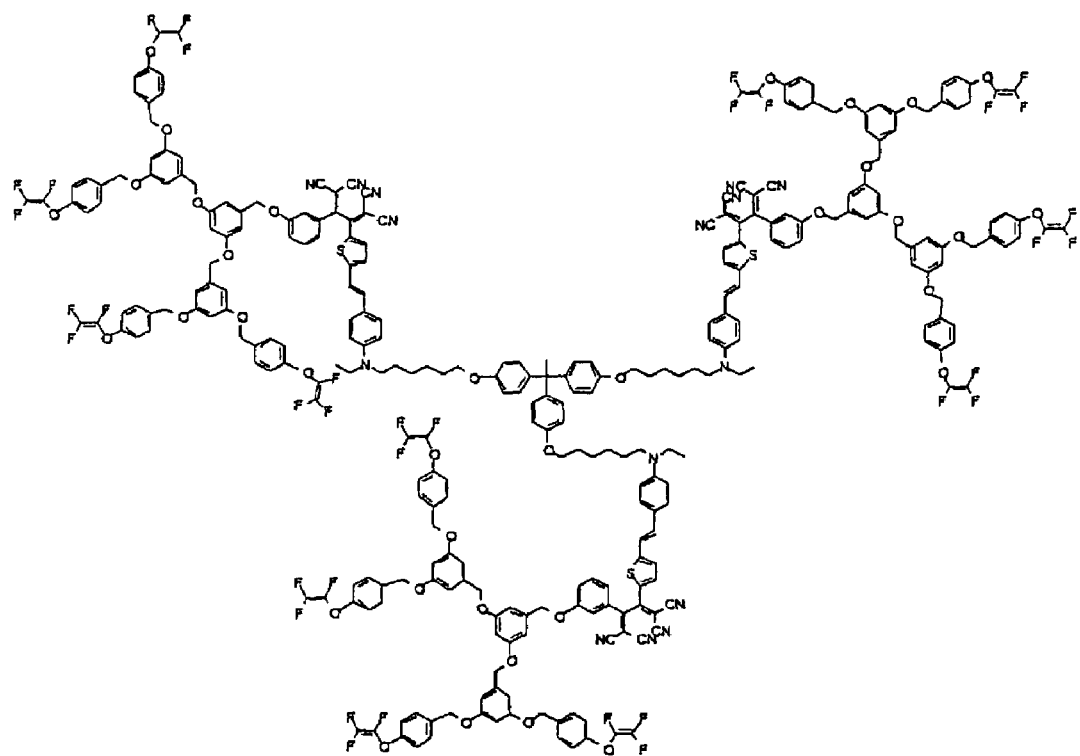
FIG. 18 is the chemical structure of a representative multi-chromophoric dendrimer of the invention.

In this example, the preparation and properties of a representative multi-chromophoric dendrimer and related macrostructure are described. The dendrimer includes trifluorovinyl ether groups and the macrostructure includes a perfluorocyclobutane-based polymer. The dendrimer is illustrated in FIG. 18.

Phenyl-tetracyanobutadienyl (Ph-TCBD) thiophene-styrene-based chromophores were developed by generating the electron acceptor in situ with the reaction between the precursor phenylacetylenes and tetracyanoethylene. The X-ray single-crystal structure of such chromophores shows that the dicyanovinylenyl moiety is linked coplanarly to the donor-substituted aryl segment and forms a push-pull system. In the structure, the phenyl-dicyanovinyl group is twisted out of the plane, which may help to prevent molecules from stacking up on each other, and thus, reduce chromophore aggregation. This, in turn, improves the poling efficiency and lowers the optical loss caused by light scattering. E-O polyquinolines incorporated with such chromophores possess very large E-O coefficient (as high as 30-60 pm/V at 1.3 to 1.55 um) and low optical loss (<2.5 dB/cm).

A representative dendrimer was prepared utilizing the Ph-TCBD-containing chromophore as the core molecule and phenyl benzyl ether as the dendrons. The space isolation of dendrimer shell further decreases chromophore-chromophore electrostatic interactions, and thus, enhances macroscopic optical nonlinearity and reduces optical loss. The representative dendrimer is illustrated in FIG. 18. The dendrimer possessed a molecular weight of 5,300 and a chromophore loading density of 29 w/w percent. The dendrimer can be direct formulated for spin coating even without pre-polymerization to form a B-staged polymer. With the dendrimer, high temperature electric-field poling results in crosslinking of the peripheral trifluorovinylether functional group to provide a macrostructure having robust mechanical properties and good temporal stability of the poling-induced polar order.

REFERENCES

Each reference cited in the application, including citations to literature and patent documents, is expressly incorporated herein by reference in its entirety.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound,

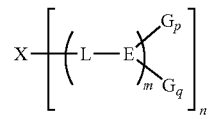

wherein n is an integer from 2 to 12; m is an integer from 1 to 8; p is an integer from 1 to 6; q is an integer from 0 to 6;

wherein X is an alkyl, heteroalkyl, or aryl group linked to E by a linker L, wherein E is a nonlinear optical chromophore moiety having the structure D-π-A, wherein D is an electron donor group, π is a conjugated bridge group, and A is an electron acceptor group, and wherein L is independently at each occurrence an alkyl, heteroalkyl, or aryl group;

wherein E independently at each occurrence is the same or different; and wherein G independently at each occurrence is a crosslinkable group.

2. The compound of claim 1, wherein n=2, m=1, p=1, and q=0.

3. The compound of claim 1, wherein n=2, m=1, p=1, and q=1.

4. The compound of claim 1, wherein n=3, m=2, p=1, and q=1.

5. The compound of claim 1, wherein n=3, m=2, p=2, and q=1.

6. The compound of claim 1, wherein n=4, m=3, p=1, and q=1.

7. The compound of claim 1, wherein G is a vinyl ether group.

8. The compound of claim 1, wherein G is a trifluorovinyl ether group.

9. The compound of claim 1, wherein A is a tetracyanobutadiene group.

10. The compound of claim 1, wherein A is a 2-dicyanomethylen-3-cyano-4,5,5-trimethyl-2,5-dihydrofuran group.

11. The compound of claim 1, wherein π is a polyene group.

12. The compound of claim 1, wherein π is a thiophene group.

13. The compound of claim 1, wherein π is a bithiophene group.

14. The compound of claim 1, wherein π is a substituted thiophene group.

15. The compound of claim 1, wherein D is an amino benzene group.

16. The compound of claim 1, wherein the linker is an alkyl group.

17. The compound of claim 1, wherein the linker is a C6 alkyl group.

18. The compound of claim 1, wherein the core is an aryl group.

19. The compound of claim 1, wherein the core is a 1,1,1-triphenyl ethyl group.

20. The compound of claim 1, wherein the core is a di(trifluoromethyl)methyl group.

21. The compound shown in FIG. 7.

22. The compound shown in FIG. 8. A compound having the structure

23. The compound shown in FIG. 9.

24. A compound shown in FIG. 10.

25. The compound shown in FIG. 18.

26. The compound of claim 1, wherein G is a dendron.

27. The compound of claim 26, wherein A is a tetracyanobutadiene group.

28. The compound of claim 26, wherein A is a 2-dicyanomethylen-3-cyano-4,5,5-trimethyl-2,5-dihydrofuran group.

29. The compound of claim 26, wherein π is a polyene group.

30. The compound of claim 26, wherein π is a thiophene group.

31. The compound of claim 26, wherein π is a bithiophene group.

32. The compound of claim 26, wherein π is a substituted thiophene group.

33. The compound of claim 26, wherein A is an amino benzene group.

34. The compound of claim 26, wherein the dendron is a phenyl benzyl ether group.

35. A film, comprising the compound of claim 1.

36. The film of claim 35, wherein the film comprises a polymer host.

37. The film of claim 36, wherein the polymer host is polyquinone.

38. A film, comprising a host material covalently coupled to the compound of claim 1.

39. The compound of claim 1, wherein n=3, m=1, p=1, and q=1.

* * * * *

UNITED STATES PATENT AND TRADEMARK OFFICE
CERTIFICATE OF CORRECTION

PATENT NO. : 7,601,849 B1 Page 1 of 1
APPLICATION NO. : 10/212473
DATED : October 13, 2009
INVENTOR(S) : K.-Y. Jen et al.

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 917 days.

| COLUMN | LINE | ERROR |
|---|---|---|
| 26 | 66 | Delete "A compound having the structure" |
| (Claim 22, | lines 1-2) | |
| 27 | 1 | "A" should read --The-- |
| (Claim 24, | line 1) | |

Signed and Sealed this

Seventeenth Day of August, 2010

David J. Kappos
*Director of the United States Patent and Trademark Office*